(12) United States Patent
DeVaul et al.

(10) Patent No.: US 7,827,011 B2
(45) Date of Patent: Nov. 2, 2010

(54) METHOD AND SYSTEM FOR REAL-TIME SIGNAL CLASSIFICATION

(75) Inventors: Richard W. DeVaul, Somerville, MA (US); Daniel Barkalow, Somerville, MA (US); Christopher Elledge, Arlington, MA (US)

(73) Assignee: Aware, Inc., Cambridge, MA (US)

( * ) Notice: Subject to any disclaimer, the term of this patent is extended or adjusted under 35 U.S.C. 154(b) by 286 days.

(21) Appl. No.: 11/986,528

(22) Filed: Nov. 21, 2007

(65) Prior Publication Data

US 2008/0162088 A1 Jul. 3, 2008

Related U.S. Application Data

(63) Continuation-in-part of application No. 11/121,799, filed on May 3, 2005, now abandoned.

(60) Provisional application No. 60/860,291, filed on Nov. 21, 2006.

(51) Int. Cl.
  *G01R 29/00* (2006.01)

(52) U.S. Cl. .................................. 702/190; 600/300
(58) Field of Classification Search ............. 702/75–76, 702/79, 189–190; 703/11, 19; 600/300–301
See application file for complete search history.

(56) References Cited

U.S. PATENT DOCUMENTS

| | | | | |
|---|---|---|---|---|
| 5,813,993 | A * | 9/1998 | Kaplan et al. ............... | 600/544 |
| 6,873,268 | B2 * | 3/2005 | Lebel et al. ............ | 340/870.16 |
| 7,285,090 | B2 * | 10/2007 | Stivoric et al. .............. | 600/300 |
| 2002/0183644 | A1 * | 12/2002 | Levendowski et al. ...... | 600/544 |

* cited by examiner

*Primary Examiner*—Eliseo Ramos Feliciano
*Assistant Examiner*—Mary C O'Malley
(74) *Attorney, Agent, or Firm*—Pierce Atwood, LLP; Joseph M. Maraia

(57) ABSTRACT

A method to achieve an accurate, extremely low power state classification implementation is disclosed. Embodiments include a sequence that matches the data flow from the sensor transducer, through analog filtering, to digital sampling, feature computation, and classification.

20 Claims, 17 Drawing Sheets

METHOD AND SYSTEM FOR REAL-TIME SIGNAL CLASSIFICATION

CROSS-REFERENCES

This application claims priority of U.S. provisional application Ser. No. 60/860,291 filed Nov. 21, 2006 and titled "System and Method for Real-Time State Classifier Development Suitable for Implementation Using Limited Embedded Computing Resources" by the present inventors.

This application is a continuation-in-part of U.S. patent application Ser. No. 11/121,799 filed May 3, 2005 now abandoned, titled "Method and System for Wearable Vital Signs and Physiology, Activity and Environmental Monitoring."

GOVERNMENT RIGHTS

This invention was derived from work partially funded by the Government under contract no. F33615-98-D-6000 from the Air Force Research Laboratory to Sytronics, Inc., and subcontract Sytronics P.O. no. 1173-9014-8001 by Sytronics to AKSI Solutions LLC. The Government retains certain rights in portions of the invention.

BACKGROUND

Many people, such as soldiers, police, fire fighters, rescue workers, etc., work under hazardous and life-threatening conditions. Many other people are at increased risk of injury or death as the result of a chronic health condition, or complications resulting from the treatment of acute illness, disability, or advancing age. Other people suffer from chronic, or at least sustained, conditions that require long-term monitoring and treatment. People in all of these circumstances may benefit from continuous monitoring, automatic real-time analysis, and proactive reporting of important changes in their health, physiology, activity state, or environmental conditions. Furthermore, those who are responsible for diagnosing, caring for, rescuing, treating, or developing medications for such individuals may also benefit significantly from such monitoring by allowing more timely, less risky, and less expensive interventions. For example, soldiers, fire fighters, rescue workers, and many other first-responders work under hazardous conditions. These individuals could benefit greatly from advance warning of hazardous environmental conditions, fatigue, illness, or other problems. Such information could allow for improved performance, the avoidance of injury or death, and the timely notification of individuals, team members, and rescue workers in the event that unusual hazards are detected or intervention is needed. Furthermore, in situations where intervention resources are limited or rescue is difficult or dangerous, this information could be invaluable for risk management and triage, allowing individuals in the field, team-members, and rescue workers to make better decisions about such matters as the deployment of human resources. By providing individuals, team-members, and rescuers with salient, timely information, everyone involved benefits from improved situation awareness and risk management.

Likewise, for those suffering from acute or chronic illness, or for those who are at elevated risk for illness or injury, the timely detection and automated reporting of life-threatening injury, disease onset, or medical complication could mean the difference between life and death. Even more valuable than the automatic detection of a crisis may be the reporting of danger signs or leading indicators that may allow a crisis to be avoided all together.

Humans respond differently to different conditions. For example, stressors such as heat and dehydration become critical at different levels for different people. Further, a person with heart disease has a different cardiovascular response that a person with heart disease. In short, people respond somewhat differently to stimuli and stressors than other people. An effective monitoring system would take this into account.

Information relevant to attempts to address these problems includes work at the U.S. Army Research Institute of Environmental Medicine (USARIEM), a part of Natick Laboratories of the United States Army. The USARIEM discloses a hand-sized monitor that miniaturizes Bruel and Kjaer instruments for measuring wet bulb and dry bulb temperature that have transformed heat risk assessment. Data from this monitor is translated to an algebraically calculated estimate of risk from heat stress for lowered productivity or work stoppage and heat prostration. This device is not based on any individual's data. That is, the device assumes that all people are the same. The device is a local monitor, lacking the proactive remote notification features.

Another device in the conventional art is the hand-held doctor project of Richard DeVaul and Vadim Gerasimov of the MIT Media Lab. The hand-held doctor includes a device having sensors for temperature, heart beating and breathing to be used to monitor a child's body. The hand-held doctor further includes infra-red connectivity to a robot which performed actions that reflected the measurements. The first and only prototype of the hand-held doctor system included a small personal Internet communicator-based (i.e., PIC-based) computer with analog-to-digital converters and a radio frequency transmitter, three hand-built sensors, a robot with a receiver, and a software program. The sensors included a thermosensor to measure body temperature, a thermistor-based breathing sensor, and an IR reflectance detector to check the pulse.

Also developed at the MIT Media Lab, the "Hoarder Board," designed by Vadim Gerasimov, had the purpose of collecting large amounts of sensor data. The board can be configured and programmed for a range of data acquisition tasks. For example, the board can record sound with a microphone add-on board or measure electrocardiographic data, breathing, and skin conductivity with a biometric daughter board. The board can use a CompactFlash device to store sensor information, a two-way radio modem or a serial port to communicate to a computer in real time, and a connector to work in a wearable computer network. When combined with a biometric daughter board or multi-sensor board, the system is capable of physiology monitoring or activity monitoring with local (on-device) data storage. The board also supported a simple low-bandwidth point-to-point radio link, and could act as a telemonitor. The board has a small amount of processing power provided by a single PIC microcontroller and a relatively high overhead of managing the radio and sensors.

Further conventional art includes products of BodyMedia Co. of Pittsburgh, Pa. BodyMedia provides wearable health-monitoring systems for a variety of health and fitness applications. The core of the BodyMedia wearable is a sensing, recording, and analysis device worn on the upper arm. This device measures several physiological signals (including heart rate, skin temperature, skin conductivity, and physical activity) and records this information for later analysis or broadcasts it over a short-range wireless link. The BodyMedia wearable is designed to be used in conjunction with a server running the BodyMedia analysis software, which is provided in researcher and end-user configurations, and in an additional configuration that has been customized for health-club use.

Other conventional wearable remote monitoring systems include alert systems that set off an alert when a condition exceeding a selected threshold is detected. One example of such a system is the Personal Alert Safety System (PASS) worn by firefighters.

It remains desirable to have a method and apparatus for wearable monitoring with real-time classification of data.

SUMMARY

The problems of monitoring individual comfortably, accurately and with the ability to generate notification of hazardous conditions with a level of confidence are solved by the present invention of a wearable monitor including real-time analysis.

Although the wearable component of the Media Lab device (the hand-held doctor) provides physiological telemonitoring capabilities (it streams raw, uninterpreted physiology data over an infrared wireless communications system) it lacks real-time analysis capabilities and accordingly does not provide proactive communications features.

The Hoarder board has a small amount of processing power and accordingly lacks real-time analysis capabilities. For example, the Hoarder board also does not provide proactive communications.

Although the BodyMedia wearable system is capable of real-time telemonitoring and at least some remote real-time analysis, the system continuously captures or wirelessly streams data in real-time to a remote location where analysis can be done.

In contrast, the present inventive technology is specifically designed for the real-time, continuous analysis of data (which may, in some embodiments of the invention, be recorded), and to proactively relay this information and analysis when dangerous or exceptional circumstances are detected. The advances of the present inventive technology include managing power consumption and communications bandwidth.

Further, those conventional systems including an alert system typically operate using simple threshold values which make them somewhat dysfunctional under real world conditions. Whether or not a hazard actually exists is often determinable only by combinations of factors and conditions. Alert systems using simple threshold values often misinterpret the data input. The Personal Alert Safety System (PASS) alarms used by firefighters are a good example of one such dysfunctional alert system. PASS alarms create a considerable nuisance with their false positive responses, and firefighters are therefore inclined to disengage them or ignore them. The problems associated with false positives may in some cases be mitigated by bringing the wearers into the interaction loop by means such as giving them the opportunity to cancel an automatically triggered call for help. This, however, only transfers the burden from one set of individuals (the rescuers) to another (the wearers). While this may reduce the economic cost of false positives it may also place an unacceptable cognitive burden on the wearer.

The present invention relates to the use of body-worn or implanted sensors, microelectronics, embedded processors running statistical analysis and classification techniques, and digital communications networks for the remote monitoring of human physiology, activity, and environmental conditions; including vital-signs monitoring; tracking the progress of a chronic or acute ailment; monitoring exertion; body motions including gait and tremor, and performance; detecting injury or fatigue; detecting environmental conditions such as the buildup of toxic gas or increasing external temperature; the detection of exposure to toxic chemicals, radiation, poisons or biological pathogens; and/or the automated detection, real-time classification, and remote communication of any other important and meaningful change in human physiology, activity, or environmental condition that may require notification, treatment, or intervention.

All of these monitoring, interpretation, and proactive communications applications have at their foundation a combination of sensing, real-time statistical analysis, and wireless communications technology. Furthermore, this technology is packaged in a manner that is as comfortable and non-invasive as possible, and puts little additional physical or cognitive burden on the user. It is robust and reliable, unobtrusive, accurate, and trustworthy. It is as simple as possible to operate, and difficult to break.

A preferred embodiment of the present invention is a wearable system including one or more small, light-weight electronics/battery/radio packages that are designed to be integrated into the wearer's current uniform, equipment, or clothing. These may be packaged as separate, special-purpose devices, integrated into existing gear (watches, cell phones, boots or equipment harnesses, pagers, hand-held radios, etc.), or incorporated directly into clothing or protective gear.

Embodiments of the present invention include an extremely low-power, low-cost real-time signal classification system suitable for implementation using minimal computing resources using the following steps in the classification process. The method includes aggressive sensor signal band limitation through analog filtering and limited sample rate and precision sampling. This obviates the need for conventional DSP signal conditioning. The method further includes feature computation prior to classification employing windowing and a mix of time- and frequency-domain methods. The use of fixed point arithmetic with carefully considered precision and dynamic range for feature computation and other operations where floating point arithmetic would conventionally be used provides efficiency. The method further includes dimensionality reduction through linear projection operation prior to model evaluation. Log representation of probabilities employing fast table-based log-space addition operations provides additional efficiency. The method further includes the evaluation discriminative or generative statistical models operating on (potentially reduced dimension) features. Embodiments of the present invention further include the use of reduced-rank (homoschedastic) representation of multivariate Gaussian (or normal) distributions where appropriate.

The result of this processing is either a set of class posterior probabilities (how likely are the various classes of interest) or a discriminative non-probabilistic classification of the signals of interest. This classification to be used to drive implementation-specific behavior of a large system.

In another embodiment of the invention, a wearable health status monitor system uses an accelerometer sensor and the classification system assesses the patterns and levels of physical activity to determine the likelihood of sickness or health, summarizes this information and reports it in a timely fashion using a body-worn wireless communications link.

In a further alternative arrangement, a wearable wellness monitor includes an accelerometer sensor. The classification system classifies exercise and rest activity states, such as counting different types of steps, determining the period of time spent walking, riding a bicycle, etc.

In a still further alternative arrangement, wearable health status monitor includes a cardiac sensor in addition to the accelerometer sensor. The classification system makes determinations of cardiac health in addition to overall sickness and health, and is equipped with a wireless emergency communications link that can summon help in the case of a cardiac emergency An alternative embodiment of the wearable health status monitor also includes a respiration sensor and can detect and report respiration-related difficulties. In an alternative arrangement, the wearable wellness monitor includes a display on the device to report summary information to the wearer while also transmitting information wirelessly to a remote receiver. In a further alternative arrangement, the wearable activity monitor classifies behavior as normal or abnormal, including falls, a complete cessation of motion, apparent writhing, crawling, etc. and includes an emergency communications link that can summon help in the case that abnormal behavior is detected.

In another embodiment of the invention, a motion classification system for an autonomous vehicle or robot uses an accelerometer sensor and a classification system that can vehicle or robot motion as normal or abnormal, including abnormal vibration, unexpected impact, or unexpected change in orientation, and also includes a GPS receiver and wireless emergency communications link that can be used to report the autonomous vehicle or robot's condition and location to a remote location. In an alternative arrangement, the motion classification system includes the application of monitoring a shipping container or package in transport. By classifying the type of conveyance (based on motion profile) and comparing that and GPS location with the expected itinerary, to detect diversion or theft in addition to mistreatment In another alternative arrangement of the present invention, the motion classification system operates in a manned vehicle with the purpose of providing an automatic distress call in the event that a crash or other abnormal event is detected. In another arrangement, a motion classification for manned vehicles uses an accelerometer sensor and the classification system for vehicle fleet management, such as the management rental cars or delivery trucks. By classifying the type of terrain driven over, the frequency of hard acceleration or sudden stops, the system allows the assessment of driver compliance with safe driving regulations without the potentially invasive recording of GPS location data.

Sensor Hub

The center of the wearable system is a sensor hub. If the wearable is monolithic, the sensor hub is a package containing all sensors, sensor analysis hardware, an appropriate power source, and an appropriate wireless communications system to proactively contact interested third parties. The sensor hub package also supports whatever wearer-interaction capabilities are required for the application (screen, buttons, microphone/speaker, etc.) For some applications, a distributed, multi-package design is more appropriate. In these cases, there is a distinguished sensor hub responsible for communicating relevant information off-body, but some or all of the sensing, analysis, and interaction is done in separate packages, each of which is connected to the central package through an appropriate personal area network (PAN) technology.

Personal Area Network

For the distributed wearable configuration, the on-body components are tied together through a personal area network. This network can range from an ad-hoc collection of sensor-specific wired or wireless connections to a single homogeneous wired or wireless network capable of supporting more general-purpose digital communications. For example, a particular wearable application may require sensors or electrodes to be placed against the wearer's skin, woven into a garment, or otherwise displaced from the sensor hub's package. In these cases, the sensors, particularly if they are simple analog sensors, are tied to the sensor hub through dedicated wired connections. In another application, for power consumption or standoff detection reasons, several digital sensing or interaction components are tied together with an on-body wired digital personal area network. In other cases, human factors or other usability constraints may make wired connections between some on-body components infeasible; in these cases, an embodiment of the present invention includes a wireless digital personal area network (RF, near-field, IR, etc.) used to tie some or all of the sensing or interaction modules to the sensor hub. Finally, further alternative embodiments of the present invention combine all three of these personal area networking strategies. In the cases where a wireless personal area network is used, all on-body modules participating in the network have an appropriate network transceiver and power source.

Sensor/Analysis Packages

In the case of a distributed, multi-package sensor design, separate packages containing sensors and sensor analysis hardware are distributed about the body as appropriate for the application and usage model. In some embodiments, these packages are analog sensors or electrodes, in which case the "package" is composed of the sensor or contact itself with any necessary protective packaging, appropriately positioned on the wearer's body or incorporated into clothing. In other embodiments, the sensor is a self-powered device with a special-purpose wireless network. In these cases the sensor package includes not only the sensor, but an appropriate transceiver, which in most cases will require a separate power supply. There are completely passive wireless sensors and radio frequency identification (RFID) systems that do not require a power supply, but instead are "powered" through the communications link. In order to conserve power and personal area network bandwidth, some versions of the inventive art will have sensor/analysis packages that combine real-time analysis hardware with the sensor in single package. This version is particularly appropriate for wireless personal area networks in which the cost-per-bit of transmitting data is significantly higher than the cost-per-bit of processing and analyzing sensor data, or in which the available wireless personal area network (WPAN) bandwidth is low. By shifting some of the processing of sensor data away from the sensor hub, lower-bandwidth "summary" or analysis data rather than raw sensor data is sent over the WPAN, thus conserving power and bandwidth.

Wearer Interaction Packages

Some embodiments include user interaction. One or more dedicated user interaction packages are thus included as part of the wearable system to improve usability. Such embodiments may include components as a screen, buttons, microphone, speaker, vibrating motor with the sensor hub or some other sensing/analysis package with an appropriately capable PAN to link it with other parts of the system. For example, in one embodiment, a display is integrated into eyeglasses, safety glasses, or an existing body-worn equipment monitor. Likewise, in another embodiment, an audio alert or interaction system is incorporated into a currently worn body-worn audio communications stem, such as a cell-phone or two-way radio. Other components and arrangements for wearer interaction are possible within the scope of the present invention. The present invention is not limited to those listed here. For example, wearer interaction can also be accomplished by writing new software or firmware modules to enable existing devices to operate with the wearable of the present invention in novel ways. Such devices include cell phones, PDAs, or other currently worn gear that support a wired or wireless communications link with the wearable sensor hub.

Packaging Considerations

One embodiment of the present invention combines a "hard" sensor hub module packaged in an ABS plastic enclosure, and one or more "soft" physiology sensing components that are in direct contact with the skin. Extra care and consideration is taken with these "soft" sensor packages that interact directly with the body. The compatibility of these sensors and their packaging is considered in view of the wearer's activities and other gear and in view of the level of distraction to the user. Improvements in the wearability are achieved when allowable and feasible by minimizing the number of "soft" sensor packages required, and by weaving sensors directly into the fabric of an undershirt, for example, or other existing clothing component.

It is important that the technology described herein is intended for long-term use, and that there is a large difference between designing for short-term wearability and long-term wearability. Many design choices that are acceptable for short-term wearability (and are found in existing biomedical sensing devices) are not acceptable for longer-term use. One example is the temporary use of adhesive electrodes for electro-cardiogram (ECG) or other bioelectrical measurement are acceptable to users, but are not well tolerated for longer-term use, such as envisioned by the technology described here. For long-term wearability, adhesive connections to the skin, prolonged contact with nickel steel or other toxic or allergenic materials, and numerous other potentially slightly irritating or uncomfortable materials or configurations are preferably avoided. Another example of a configuration preferable avoided is the temporary use of a highly constraining and somewhat rigidified under-shirt that holds sensors close to the body at the cost of distraction and the inability to move normally. Instead, as discussed above, sensors are ideally woven into normal attire.

The size, weight, and positioning of the "hard" components is a consideration for wearability and usability. Reducing size and weight as much as possible is important, but robustness and compatibility with an appropriate range of activities and existing gear is also important. Positioning hard components on the body is an important factor effecting comfort, especially for wearers who are otherwise encumbered. Wired connections on the body and the mechanical connections associated with them present certain reliability and robustness challenges. They also present challenges in wearability and usability. In applications using the technology described herein, various embodiments include strain relief to protect the cables and wired connections. Frequently made or broken mechanical connections are designed for extreme durability. At the same time, heavy or bulky connectors—which may be required for applications involving gloved users—are selected to minimize the impact on wearability. For these reasons, it is desirable to minimize the number of wired connections and mechanical interfaces for body-worn applications.

The present invention together with the above and other advantages may best be understood from the following detailed description of the embodiments of the invention illustrated in the drawings, wherein:

DRAWINGS

DESCRIPTION

Figure 1:
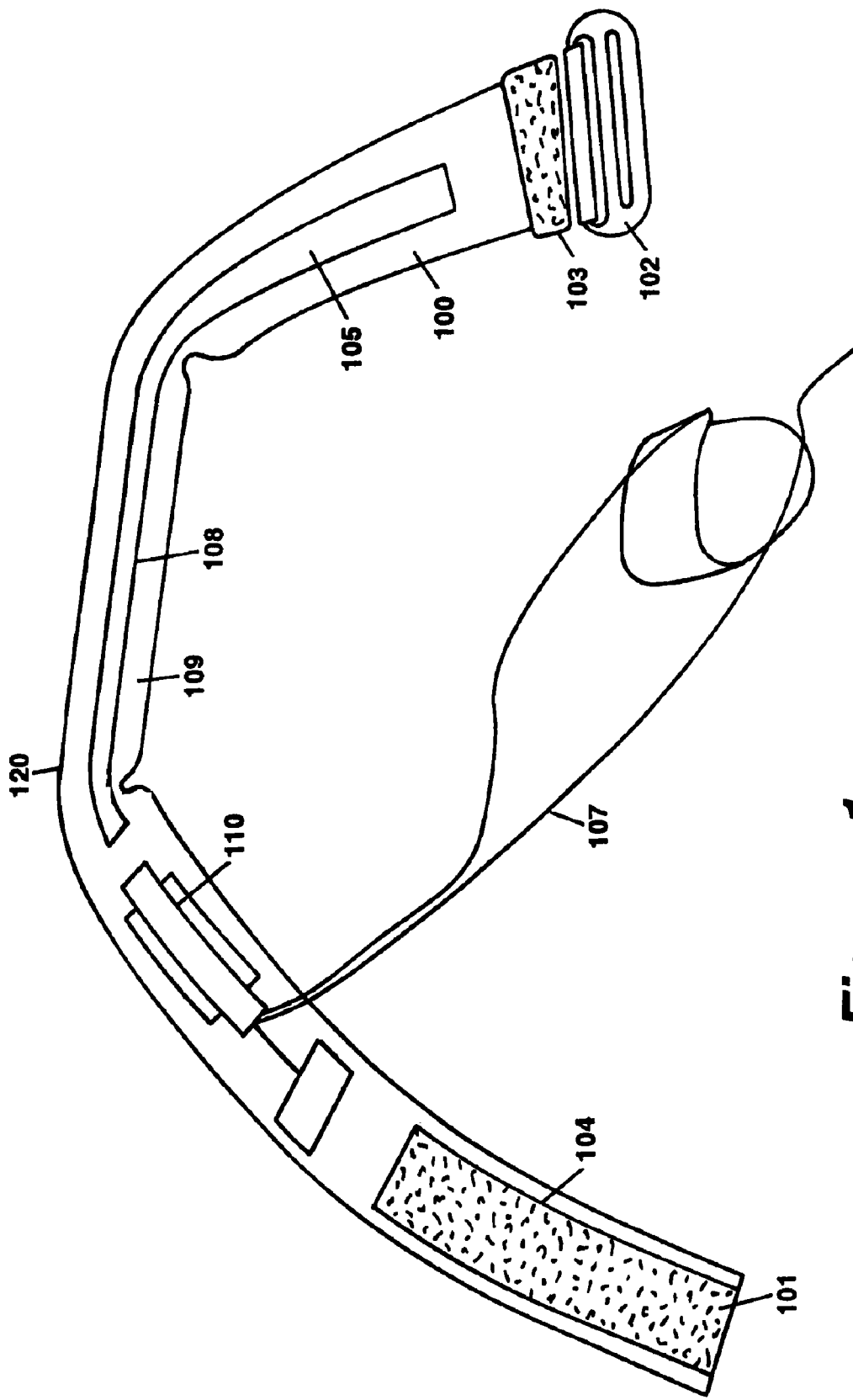
FIG. 1 is a picture of a chest strap according to principles of the invention.

A remote monitoring system includes a wearable configuration of sensors and data analysis devices and further includes data models for interpretation of the data collected by the sensors. The sensors monitor human physiology, activity and environmental conditions. In one embodiment, the data analysis devices use the data models to determine whether hazardous conditions exist. A communications system included in the remote monitoring system sends an alarm when the remote monitoring system detects a hazardous condition. Embodiments of the present invention include a method of implementing a real-time state classification system suitable for a range of embedded systems applications, including wearable health, activity, and environmental state monitoring, the monitoring of vehicles, aircraft, robots, and industrial equipment, and many other situations in which it is desirable to employ intelligent sensor systems to determine the state of some larger, complex system. The method minimizes the size, weight, cost, and power consumption of the classification system, making it suitable for a wider range of applications than would be possible with a conventional approach, particularly in the domain of body-worn applications or embedding in existing battery-powered consumer gear, such as cell phones, music players, PDAs, etc. The method is also particularly well suited for medical device applications, including both body-worn and implanted medical applications.

All of these monitoring, interpretation, and proactive communications applications have at their foundation a combination of sensing, real-time statistical analysis, and wireless communications technology. Furthermore, this technology is packaged in a manner that is as comfortable and non-invasive as possible, and puts little additional physical or cognitive burden on the user. It is robust and reliable, unobtrusive, accurate, and trustworthy. It is as simple as possible to operate, and difficult to break. A feature of the system described here is the proactive, robust notification capability provided by the combination of sensing, real-time statistical analysis, and proactive communications. This capability makes it possible to automatically and reliably notify relevant third parties (care-givers, rescuers, team-members, etc.) in the event of emergency or danger.

The body-worn, implanted, and mobile components of the system (hereafter "the wearable") are highly reliable with long battery (or other mobile power-source, e.g. fuel cell) life, so that both the individual being monitored and those who may be required to intervene can rely on its continued operation over a sufficiently long period of time without the constant concern of power failure. To achieve this, an appropriate power source is selected and the electronics are engineered for low power consumption, particularly for processing and communications. Effective low-power engineering involves careful selection of electronic components and fine-grained power management so that particular subsystems (such as a communications radio, microprocessor, etc.) may be put into a standby mode in which the power consumption is reduced to an absolute minimum, and then awakened when needed.

Human Factors

The human factors of the wearable—both cognitive and physical—are important to the overall usefulness of the system. From the cognitive standpoint the wearable is simple to use, with as many functions as possible automated, so that the wearer can attend to other tasks with minimal cognitive burden imposed by the device. To the extent that the wearable interacts with the user, the interactions are carefully designed to minimize the frequency, duration, and complexity of the interactions. The physical human factors of the wearable are also important; the wearable's physical package is as small and light as possible, and is carefully positioned and integrated with other body-worn (or implanted) elements so that it will not encumber the user, interfere with other tasks, or cause physical discomfort. Sensors, in particular physiological sensors, are carefully selected and placed for measurement suitability, compatibility with physical activity, and to minimize the physical discomfort of the wearer. Weight and size are important design criteria, requiring both miniaturization of electronics and careful low-power design, since power consumption translates directly into battery (or other mobile power source) weight.

Sensing

Not all locations on the human body are equal with regard to the location of physiological sensors, and in many cases it may be desirable to embed sensors or other components of the system in clothing, shoes, protective gear, watches, prosthetics, etc. Wired connections among distributed on-body wearable components are, at times, infeasible due to human factors or usage constraints, and in such cases a suitable wireless personal-area network is integrated that meets the bandwidth, latency, reliability, and power-consumption requirements of the application. Likewise, a suitable local- or wide-area wireless networking technology has been chosen so that the wearable components of the system may communicate with care givers, rescue workers, team members, or other interested parties.

In many cases, a plurality of sensors are appropriate to measure a signal of interest. In some cases no appropriate single sensor exists. For example, there is no single sensor that can measure mood. In others, constraints of the body-worn application make such sensing impractical due to ergonomic considerations or motion artifacts arising from the ambulatory setting. For example, measuring ECG traditionally requires adhesive electrodes, which are uncomfortable when worn over an extended period. Core body temperature is most reliably sensed by inserting probes into body cavities, which is generally not comfortable under any circumstances. Those skilled in the art will recognize that many additional examples could be identified. In some cases these problems can be mitigated through improved sensor technology (e.g. replacing adhesive electrodes with clothing-integrated fabric electrodes for ECG, or the use of a consumable "temperature pill" for core-body temperature measurement). In other cases, however, a constellation of sensors is applicable. The constellation of sensors parameterize a signal space in which the signal of interests is embedded, and then use appropriate signal processing and modeling techniques to extract the signal of interest.

In some embodiments, the constellation of sensors measure a collection of signals that span a higher-dimensional measurement space in which the lower-dimensional signal of interest is embedded. In these alternative embodiments, the lower-dimensional signal of interest is extracted from the higher-dimensional measurement space by a function whose domain is the higher-dimensional measurement space and whose range is the lower-dimensional measurement space of interest. This function involves, for example, a sequence of operations which transform the representation of the original measurement space. The operations further include projecting the higher-dimensional space to a lower-dimensional manifold, partitioning the original or projected space into regions of interest, and performing statistical comparisons between observed data and previously constructed models.

Automated Real-Time Interpretation of Sensor Signals

Throughout this discussion the general term "model" or "model/classifier" is used herein to describe any type of signal processing or analysis, statistical modeling, regression, classification technique, or other form of automated real-time signal interpretation. Even in situations where the signal of interest is measurable in a straightforward manner that does not burden or discomfort the user, the proper interpretation of this signal may require knowledge of other signals and a the wearer's personal history. For example, it is relatively straightforward to measure heart rate in an ambulatory setting, and increases in heart rate are often clinically meaningful. Simply knowing that the wearer's heart rate is increasing is generally not sufficient to understand the significance of this information. With the addition of information about the wearer's activity state (which can be extracted from the analysis of accelerometer signals) it is possible to distinguish an increase in heart-rate resulting from increased physical activity from one that is largely the result of emotional state, such as the onset of an anxiety attack. Likewise, the cardiovascular response of a fit individual will differ substantially from that of an unfit person. Thus, even for interpreting a relatively straightforward physiological signal such as heart rate, proper interpretation may require additional sensor information as well as additional information about the wearer.

Noise and Uncertainty

Just as measured signals typically contain noise, interpretation typically involves uncertainty. There is a great deal of difference between saying "it is going to rain" and "there is a 35% chance of rain." Likewise, there is a large difference between an automated interpretation with high confidence and one with low confidence. One source of uncertainty in the interpretation of sensor signals is noise in measurement. Measurement typically involves some degree of noise, and the amount of noise present varies depending on circumstances. For example, many physiological sensors are prone to motion artifacts, and in such cases the amount of noise in the signal is strongly correlated with the amount of motion. Another source of uncertainty lies in the limitations of what can be sensed and modeled—not all relevant parameters can be measured or even known for some important conditions. For example, after decades of research and modeling, the US Army recently discovered when trainees died of hypothermia in a Florida swamp that there was greater variation among various individuals' thermoregulatory capacities than had been previously believed.

In general, models capable of working with and expressing uncertainty are preferable to those which are not. Further, regardless of whether the sensing task is simple or complex, all sensor measurements are a combination of signal and noise, and appropriate analysis techniques takes this into account. Although linear regression, thresholding or other simple modeling and classification techniques may be appropriate for some applications, better results can almost always be obtained through the application of more principled statistical modeling techniques that explicitly take uncertainty into account. This is particularly important for the automated classification of conditions, events, or situations for which there is a high cost for both false-positive and false-negative classification. For example, the failure of a system designed to detect life-threatening injury, cardiac fibrillation, etc. may be life-threatening in the case of a false negative, but expensive and ultimately self-defeating if false positives are common. The Personal Alert Safety System (PASS) alarms presently used by firefighters are a good example of one such dysfunctional alert system because they create a considerable nuisance with their false positive responses, and firefighters are therefore inclined to disengage them or ignore them. The problems associated with false positives may in some cases be mitigated by bringing the wearers into the interaction loop by means such as giving them the opportunity to cancel an automatically triggered call for help. This, however, only transfers the burden from one set of individuals (the rescuers) to another (the wearers). While this may reduce the economic cost of false positives it may also place an unacceptable cognitive burden on the wearer.

Statistical Classification Process

Figure 8:
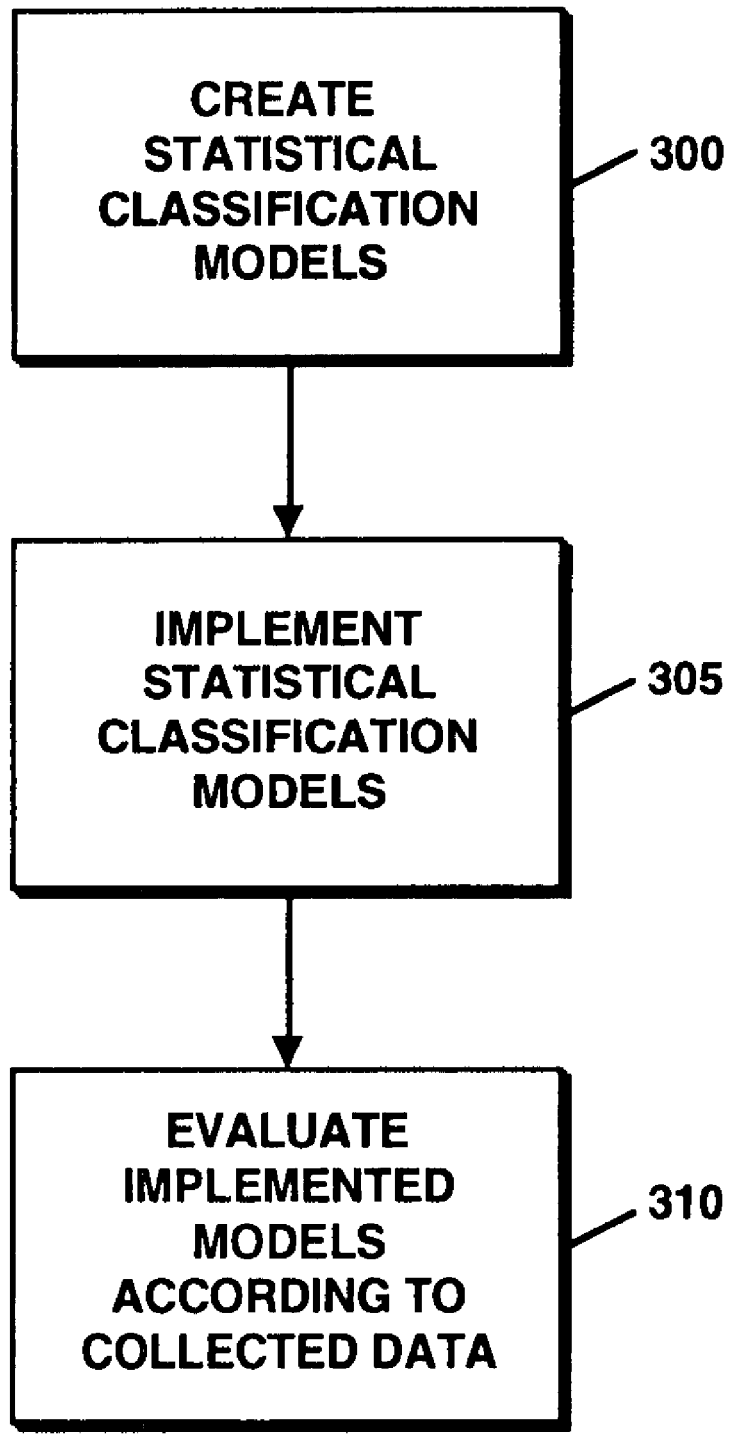
FIG. 8 is a flow chart of the statistical classification process according to principles of the invention.

FIG. 8 is a flow chart of a statistical classification process according to principles of the invention. Statistical classification is the process by which measured sensor data is transformed into probabilities for a set of discrete classes of interest through the application of statistical classification techniques. The application of the process summarized here to the problem of wearable telemonitoring systems is one of the key innovations embodied in the inventive system. At step 300, an appropriate set of statistical classification models is created (hereafter to be called "model creation"). At step 305, the statistical classification models resulting from the model creation step are implemented on the wearable such that they can be evaluated in real-time using on-body computational resources ("model implementation"). At step 310, the wearable telemonitor system evaluates these models in real-time using live sensor data, the results of which may trigger communications with remote third parties, cause delivery of status information to the wearer, or otherwise play an important role in the behavior of the wearable telemonitor system. This is the "model evaluation" step.

Model Creation

In general, model creation (step 300) is done once for each class of problem or individual user. In alternative embodiments of the invention, the model is continually refined as the models are used (referred to as "on-line learning"). Unless on-line learning is needed, the model creation process can be done off-line, using powerful desktop or server computers. The goal of the model creation process described here is to create statistical classification models that can be evaluated in real-time using only on-body resources.

Model creation starts with data gathering. In one embodiment of the invention, data is gathered through body-worn sensor data. In general, this data is "labeled" so that what the data represents is known. In some embodiments of the invention, there are two data classes, such as "normal heart activity" and "abnormal heart activity." Actual example data from both classes is gathered, although there are situations where simulated data may be used if the acquisition of real data is too difficult, costly, or poses some ethical or logistical challenges. From analysis of this representative data, appropriate modeling features are chosen to be used by the model Features are derived measurements computed from the "raw" sensor data. For example, derived measurements in one embodiment are created by computing the differential forward Fourier transform (DFFT) or power spectrum from a short-time windowed sequence of data. Features may also be derived by bandpass filtering, signal integration or differentiation, computing the response of filterbanks or matched filters or other signal processing operations. A "trial feature" is a trial operation which is used to test possible model correlations. The analysis process typically includes the computation of several trial features in order to arrive at a final model feature. After features are chosen, an appropriate model type and structure is chosen. Finally, the parameters for the specific model type, structure, and representative data are estimated from the representative data.

In a first example of an application of the present invention, the sensors are used to measure core body temperature and the data model is the likelihood of morbidity due to heat injury. In this example, the collected data can be analyzed directly according to the morbidity model in order to make conclusions about the severity of the injury.

A second example application of the present invention is a cardiac fitness meter using the cardiac interbeat interval (IBI) at rest to determine cardiac fitness of a subject. A system measuring the duration between heart beats is used to determine the IBI. In order to validate this fitness meter, it is examined against an established, widely recognized fitness assessment system such as a cardiac stress test on a treadmill. An appropriately representative study population is selected which can be done using known techniques in experimentation and statistics. Several minutes of IBI data for each subject at rest is then recorded which results in, for example, two hundred numbers. Then, the subjects are evaluated using the treadmill stress test to establish which subjects are "fit" and which are "unfit," thus creating model labels. In this example, the "labels" are a continuum, but data cut-offs can be established for analysis purposes. One example of a data cutoff in this instance is the Army minimum fitness standard. Thus, for each subject, the trial feature is computed from the measured interval data. The trial feature (i.e., the IBI variance) is then plotted against the labels, "fit" and "unfit." An effective fitness meter results in a clear correlation between a higher IBI variance and the "fit" label.

The above examples are simplified, however, the examples demonstrate the point that trial features can be used to construct models to be used with high confidence when using complex, high-dimensional data showing large variations over time or including noise or uncertainty.

Model Implementation

The results of the model creation step (step 300)_are: (1) the process for calculating model features, (2) the structure and type of the model, and (3) the model parameters themselves. These three elements specify the statistical classifier. Implementing a model evaluation system (step 305) that is capable of evaluating the statistical classifier in real-time using on-body resources is technically challenging. Feature calculation and model class posterior calculation (i.e., calculating the likelihood that an observed feature, or set of features, is modelable by a particular model class) can be computationally intensive. Although it is often possible to do these calculations using basic computing resources such as inexpensive microcontrollers, doing so requires the careful selection of appropriate computational resources as well as highly optimized software implementations. A component of this is choosing appropriate algorithms and then implementing them using optimized fixed-point arithmetic. For example, the preferred embodiment includes a very fast algorithm for calculating the Fast Fourier Transform of the sensor data using fixed-point arithmetic rather than floating point arithmetic, because a floating point algorithm would be too slow on a microcontroller.

Model Evaluation

The results of model creation and implementation are a system capable of classifying "live" sensor data in real-time using on-body resources. The step of classification (step 310) entails real time comparison of the features calculated from a data stream to the parameters of the model. This matching using Bayesian statistics identifies the "activity" with which the data stream best matches and yields a statistical estimate of the confidence with which the match can be made. The results of this classification process drive the proactive communications features of the wearable and may otherwise complement information acquired from the wearer, from the wearer's profile or history, and from the network in driving application behavior. An example of model evaluation is described below with regard to FIG. 7A and FIG. 7B.

Distributed vs. Monolithic Wearable Signal Interpretation Architecture—Bandwidth and Power Consumption The wearable provides sufficient processing power to implement whatever modeling or classification system is necessary for the application. This processing power is provided by local, on-body computing resources, without depending on external computation servers. Modern microcontrollers and low-power embedded processors, combined with low-power programmable digital signal processors (DSPs) or DSP-like field programmable gate arrays (FPGAs), provide more than enough processing power in small, low-power packages suitable for most on-body applications. Applications which require distributed on-body sensing may also require on-body distributed computation. Accordingly, in those embodiments with distributed on-body sensing, power at the one or more computational centers on the body and personal area network bandwidth consumption are reduced by performing as much signal processing and modeling as possible in the same package as the sensor. This is particularly important in higher-bandwidth distributed sensing applications (such as distributed wearable systems that employ computer vision systems or speech recognition) in which the raw signal bandwidth may strain the capabilities of the personal area network. In addition, even low-bandwidth distributed sensing applications may benefit from distributed processing since the power cost of wireless communications is almost always higher than computation in modern hardware.

Having the capability to process information on-body is supplemented by the ability to send either the products of the analysis or the original raw data, optionally mediated by the results of on-body analysis, to other locations for further analysis or interpretation of data at a location remote from the body. Indeed, the capability to relay raw sensor signals (be they physiological data, environmental conditions, audio or video, etc.) to remote team members, care givers, or rescuers may be important to the planning and execution of an appropriate intervention. As such, the distributed processing model need not be confined to on-body resources, as the wearable supports a local- or wide-area wireless networking capability in order to be able to communicate with other team members, care givers, rescuers, etc. Such communications are expensive in terms of power consumption, and are generally not preferable for routine operation. If, however, the local- or wide-area communications system is being used for other purposes (such as to call for help, or to provide a "back haul" voice communications channel, etc.) this channel can be important to push data out to "heavy weight" processing resources such as remote computer servers. These servers can be used to provide more sophisticated analysis to the remote team or caregivers. They can also be used to provide additional analysis or interaction capabilities to the wearer (such as a speech-based interface), or to allow for real-time adaptation or modification of the on-body modeling or classification system, including firmware updates and the fine-tuning of model parameters. Those skilled in the art will recognize that the precise computational functionality that is performed, and which of it is performed on the body versus remotely will evolve over the years as microcontrollers become smaller, more powerful and less expensive, and as the applications evolve in purpose and implementation.

Reconfigurable Wearable Signal Interpretation Hardware

Since a single set of sensors can potentially be used for many applications, and because models may be improved over time or tailored to the needs of specific individuals (or even be continuously improved through on-line learning techniques) it is important that the signal processing and interpretation hardware be adaptable. In the preferred embodiment, it is to alter model/classifier parameters, change the model structure or type, or add additional models to be evaluated by updating the wearable's software or firmware, without the need to modify or replace hardware. This is accomplished through the use of self-reprogrammable microcontrollers or conventional embedded/mobile processors (the Intel XScale is an example of one such processor). Alternative embodiments use high-performance reconfigurable signal processing hardware for some or all of the computation, such as programmable DSPs or FPGAs.

Human Machine Interaction

Any explicit interaction demands that the wearable imposes on the wearer will typically translate directly into increased cognitive load and likely decreased task performance. This effect has been documented prior to the development of wearable computers in the form of competing tasks experiments in cognitive psychology. As a result of this phenomenon, it is important to design the human-machine interaction system of the wearable to minimize the frequency, duration, and complexity of these demands. Donald Norman's "Seven Stages of Action" provide a useful framework in which to begin to analyze interaction demands. The seven stages of action are: 1. Forming the goal; 2. Forming the intention; 3. Specifying the action; 4. Executing the action; 5. Perceiving the state of the world; 6. Interpreting the state of the world; and 7. Evaluating the outcome. *The Design of Everyday Things*, Donald A. Norman, Currency-Doubleday, New York, 1988, pp. 46-48. In particular interactions are carefully designed to minimize Norman's gulfs of evaluation and execution. id., pp. 49-52.

In many cases needed information gathered through explicit interaction with the user can be replaced with information gathered from the automated interpretation of sensor data, augmented with previously stored information and information available through wireless networks. For example, the wearer need not provide location information to rescuers because the information is already available through technologies built into some of the alternative embodiments of the inventive system: a GPS receiver, a dead reckoning system, an RF signal map, or other automated source, taken individually or in some combination. Using information acquired from other sources to reduce the need for explicit user interaction is an important part of mitigating the cognitive demands imposed by the wearable on the wearer, but does not address the entire problem. Interactions that deliver information to the wearer may interfere with other tasks, even when no explicit input is required. Making such information easily understood—reducing Norman's "gulf of evaluation"—is important for reducing the cognitive demands of such interactions. Presenting the wearer with stimuli that require a decision typically interferes with other decision-making tasks. As a result, in the disclosed art any wearable interactions are designed to minimize the presentation of stimuli that require that the wearer make a decision. For example, it would be unreasonable to ask of an airman to remember to turn on his life signs device when he was also involved with making decisions about escaping from a life-threatening situation. Thus, when the device is donned prior to a mission and used with sensors and algorithms to determine whether an airman is alive or dead, it has sufficient battery storage so that it is automatically on and stays on until the airman returns to friendly territory. There is no decision required by the airman to turn it on.

Compatibility with Existing Procedures, Networks, and Equipment

The wearable application is designed for the greatest possible compatibility with existing procedures, activities, and gear used by the wearer. This is important both for reducing the additional training required for effective use of the wearable and to decrease the complications, inconvenience, and expense of adopting the wearable technology. For military and industrial applications this means that the wearable has been designed to function with standard radio gear and networks, standard or existing communications protocols, normal emergency procedures, etc. By leveraging standard body-worn elements such as hand-held radios for long-range communications or personal digital assistants (PDAs) for user interaction, the overall weight, bulk, and complexity of the wearable system is reduced as well.

For civilian biomedical applications, this means that the wearable is designed as much as possible to be unobtrusive, to be compatible with the widest range of street clothing and routine user activities, and to work with (or replace) conventional body-worn devices such as cell phones, PDAs, etc.

Example Embodiments

Below are described example embodiments of the inventive art constituting the hub, including a variety of alternative embodiments constituting the hub with sensors, peripherals and communications. One embodiment contains its own radio with a range of about 50-100 yards. Another embodiment ties to an electronic device that provides communications to third parties. In another alternative embodiment, a life signs monitor for military personnel uses one of these hubs with sensors to measure heart rate, breathing pattern, GPS (global positioning system), and a three-dimensional accelerometer to measure motion, with selective data sent on demand to an authorize receiver. In another alternative embodiment, a Parkinson's monitor to measure dyskinesia and gait as a means to estimate the need for medication, uses one of the two same hubs, plus accelerometers placed on selected extremities for a period varying from 1 hour to 24 or more hours, with data stored in flash memory or streamed to a separate computer. Still further alternative embodiments employ other combinations of sensors. Those skilled in the art will recognize that the inventive art will support many variations of these same hub, sensor, communications, and linkage configuration for varying purposes. For example, a monitor employing a plurality of sensors can determine a degree of progression of Parkinson's disease or other neurological condition such as stroke or brain lesion that effects for example gait or motion of a patient. Another example monitor according to principles of the invention determines an adverse reaction to, or overdose of, a psychotropic medication. In a further example, a monitor determines the presence and degree of inebriation or intoxication. Still further alternative embodiments includes a monitor that detects a sudden fall by the wearer or an impact likely to cause bodily trauma such as a ballistic impact, being struck by a vehicle or other object, or an explosion in the proximity of the wearer. Still further alternative embodiments include a monitor to determine an acute medical crisis such has a heart attack, stroke or seizure. In one alternative arrangement, the monitor is able to detect a panic attack or other acute anxiety episode. In a further alternative arrangement, the monitor is able to determine from for example unsteady gait or reduced activity that there is frailty, illness or risk of medical crisis. In another alternative embodiment of the invention, the monitor is capable of detecting hazards to which the wearer has been exposed such as biological pathogens, neurotoxins, radiation, harmful chemicals or toxic environmental hazards.

FIG. 1 is a picture of a chest strap holding sensors according to the present invention. The chest strap 120 holds sensors securely in proximity to the torso of a person (not shown). Sturdy cloth 100 forms the backbone of the chest strap 120, with soft high-friction cloth 105 placed on the inside to contact the skin of the torso so that the chest strap is optimally held in position. Should this not be sufficient, shoulder straps (not shown) can be attached to provide over-the-shoulder support. The chest strap 120 is cinched to appropriate tightness using a buckle 102 through which the opposite end 101 of the chest strap is fed.

Figure 2:
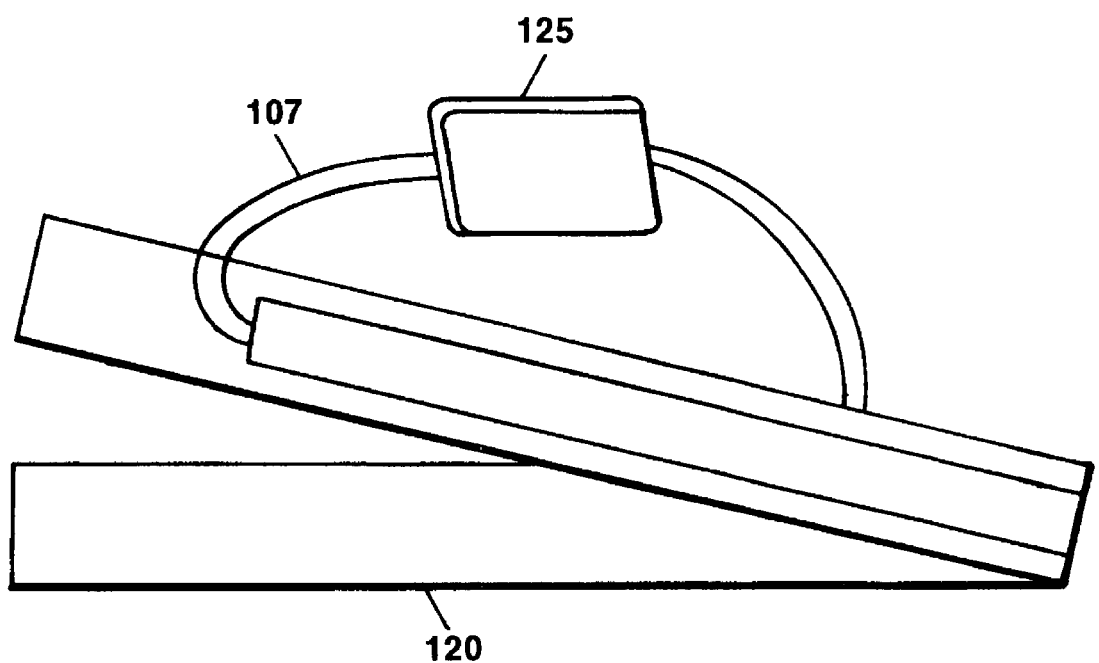
FIG. 2 is a picture of a chest strap including wires to a hub according to principles of the invention.

The hooks 103 and eyes 104 of Velcro complete the secure, non-moveable linkage. Wires 107 are used to link one or more sensors in the chest strap 120 to a hub 125, as shown in FIG. 2. The wires 107 emerge from conduits in the chest strap 120 leading from pockets or other topological features that hold or otherwise constrain the position of the sensors. Elastic cloth 109 with a spring constant much less than that of a piezo-electric strap 108 provides surrounding surface and structural strength as well as consistent look and feel for that part of the strap. The piezo-electric strap 108 increases and decreases voltage as it is stretched by the user's breathing out and in, thus provides a signal that can be used to determine whether the user is breathing, and if so, certain of the characteristics of that breathing. A pocket 110 holds a Polar Heart Monitor or other R-wave detector or other non-obtrusive heart beat detector, which communicates detailed information about heart beats wirelessly or by wire to the hub 125 (shown in FIG. 2), which is attached by Velcro or by other means to the outside of the chest strap, or to another on-body location. Alternative embodiments of the invention use radio communications to connect the sensors in the chest strap 120 to the hub 125 and so do not require the wires 107.

Figure 3:
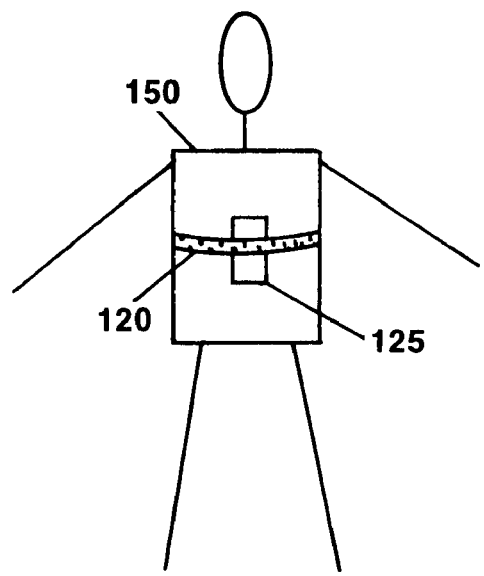
FIG. 3 is a block diagram of a first configuration of the hub and sensor placement on a representative human figure according to principles of the invention.

FIG. 3 is a block diagram of a first configuration of the hub and sensor placement on a human figure representation 150 according to principles of the invention. The human figure representation 150 is shown wearing a chest strap 120 having sensors (not shown) and a hub 125. The sensors include, for example, a piezoelectric breathing sensor and a polar heart monitor. The hub 125 includes, for example, an accelerometer and analytics. This example configuration of sensors can be used to monitor a patient with Parkinson's disease where pulmonary data, cardiovascular data and motion data are of interest.

Figure 4:
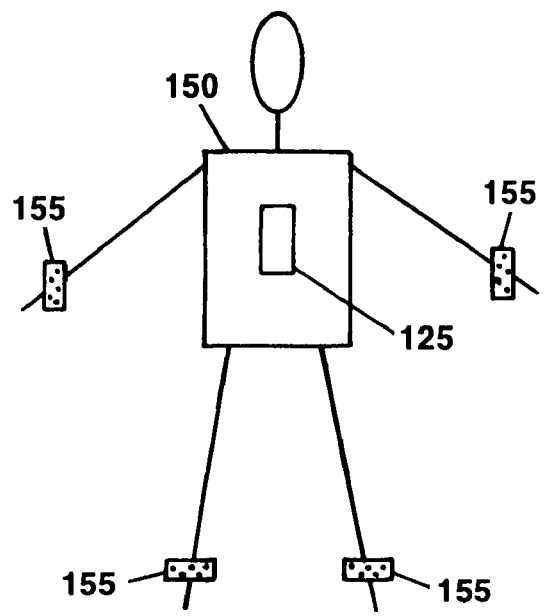
FIG. 4 is a block diagram of a second configuration of the hub and sensor placement on a representative human figure according to principles of the invention.

FIG. 4 is a block diagram of a second configuration of the hub and sensor placement on a human figure representation 150 according to principles of the invention. The human figure representation 150 is shown wearing a hub 125 at the torso and sensors 155 at the wrists and ankles. The hub 125 includes, for example, an accelerometer and a wireless personal area network. The sensors are, for example, accelerometers and may include analytics. The sensors communicate wirelessly with the hub 125 through the wireless personal area network.

Figure 5:
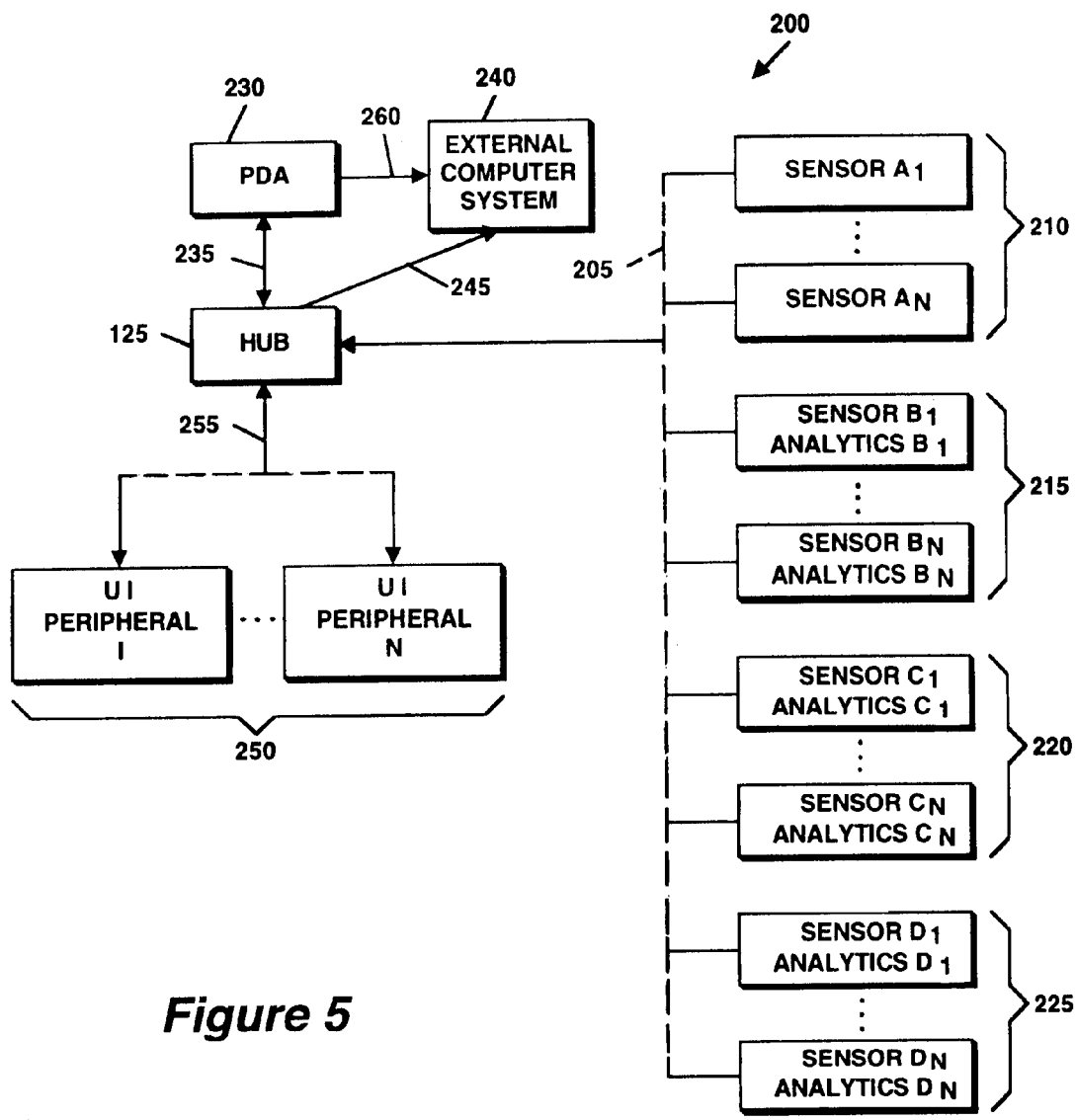
FIG. 5 is a block diagram of a hub and sensor network according to principles of the invention.

FIG. 5 is a block diagram of the hub and sensor network 200 according to the present invention. The hub and sensor network 200 includes a hub 125 connected through a first wired or a wireless personal area network (PAN) 205 a variety of sensors 210, 215, 220, 225. Sensors A 210 are without proactive communications abilities and instead are polled for data by the hub 125. Sensors B 215 are without proactive communications abilities however do include analytics. Sensors C 220 include both proactive communications and analytics. Sensors D 225 include proactive communications but are without analytics. The hub 125 is also connected to a PDA 230, or some other portable wireless communications device such as a cell phone, through a second wireless network 235. The hub 125 is further connected to an external local area network (LAN) or external computer system 240 through a wired or wireless connection 245. The hub 125 is still further connected to user interface peripherals 250 through a wired or wireless connection 255. The PDA 230 and external computer system 240 are connected through a wired or wireless connection 260.

In operation, the hub 125 communicates with and controls the sensors 210, 215, 220, 225, directing the sensors 210, 215, 220, 225 to collect data and to transmit the collected data to the hub 125. Those sensors 220, 225 with proactive communications send collected data to the hub 125 under preselected conditions. The hub 125 also communicates with and controls the user interface peripherals 250. The hub 125 further communicates with portable devices such as the PDA 230 and with external network or computer systems 240. The hub 125 communicates data and data analysis to the peripherals 250, portable devices 230 and external systems 240.

The hub and sensor network 200 shown here is merely an example network. Alternative embodiments of the invention include a network 200 with fewer types of sensors, for example, including a network 200 with only one type of sensor. Further alternative embodiments include a network 200 with a hub 125 connected to only a PDA 230. In still further alternative embodiments, the various devices in the network 200 are able to communicate with each other without using the hub as an intermediary device. In short, many types of hub, sensor, communications devices, computer devices and peripheral devices are possible within the scope of the present invention. The present invention is not limited to those combinations of devices listed here.

Sensor Hub Module with Internal Radio

Figure 6A:
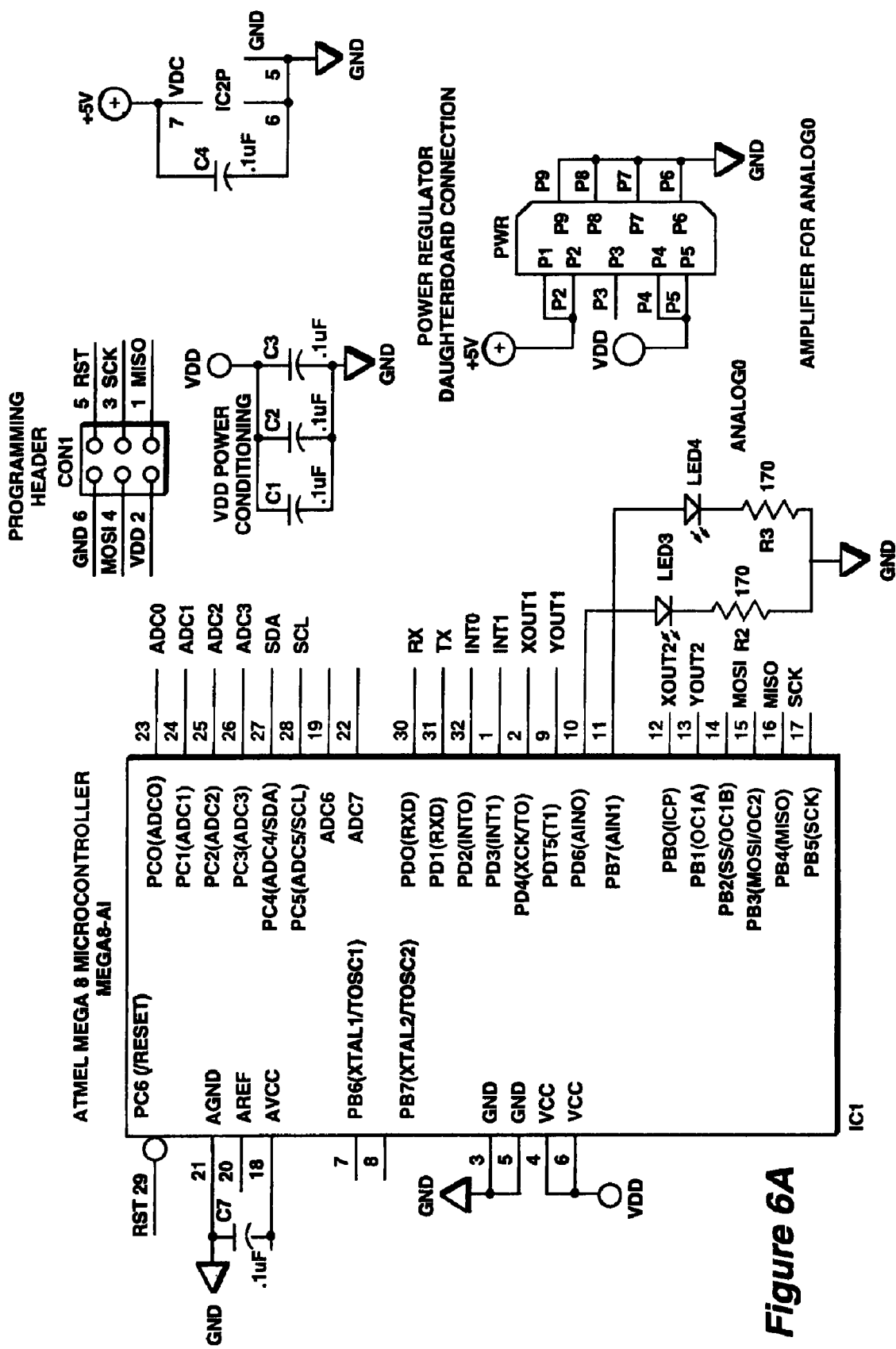
FIG. 6A is a schematic diagram of a first portion of a first hub according to principles of the invention.
Figure 6B:
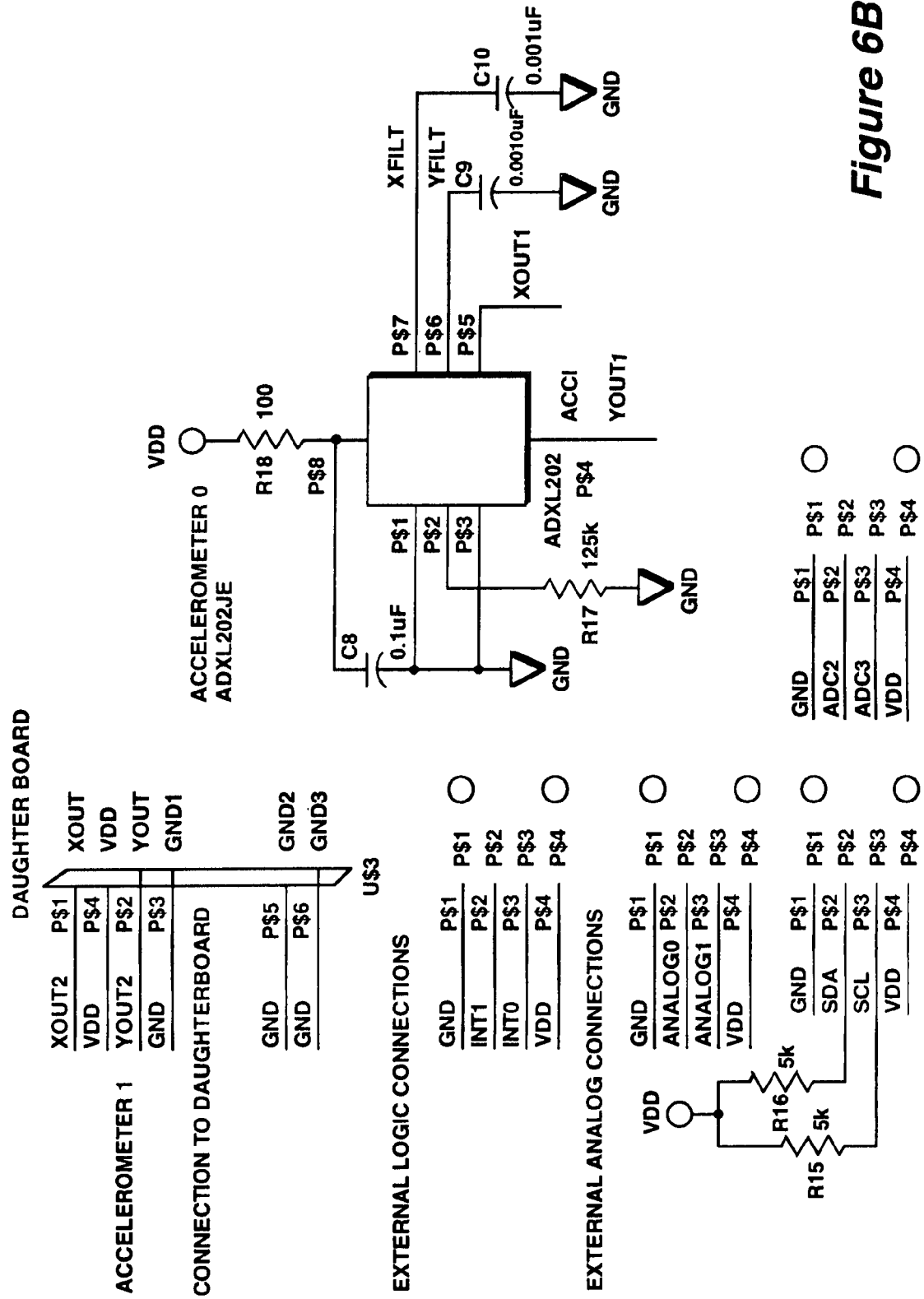
FIG. 6B is a schematic diagram of a second portion of the first hub according to principles of the invention.
Figure 6C:
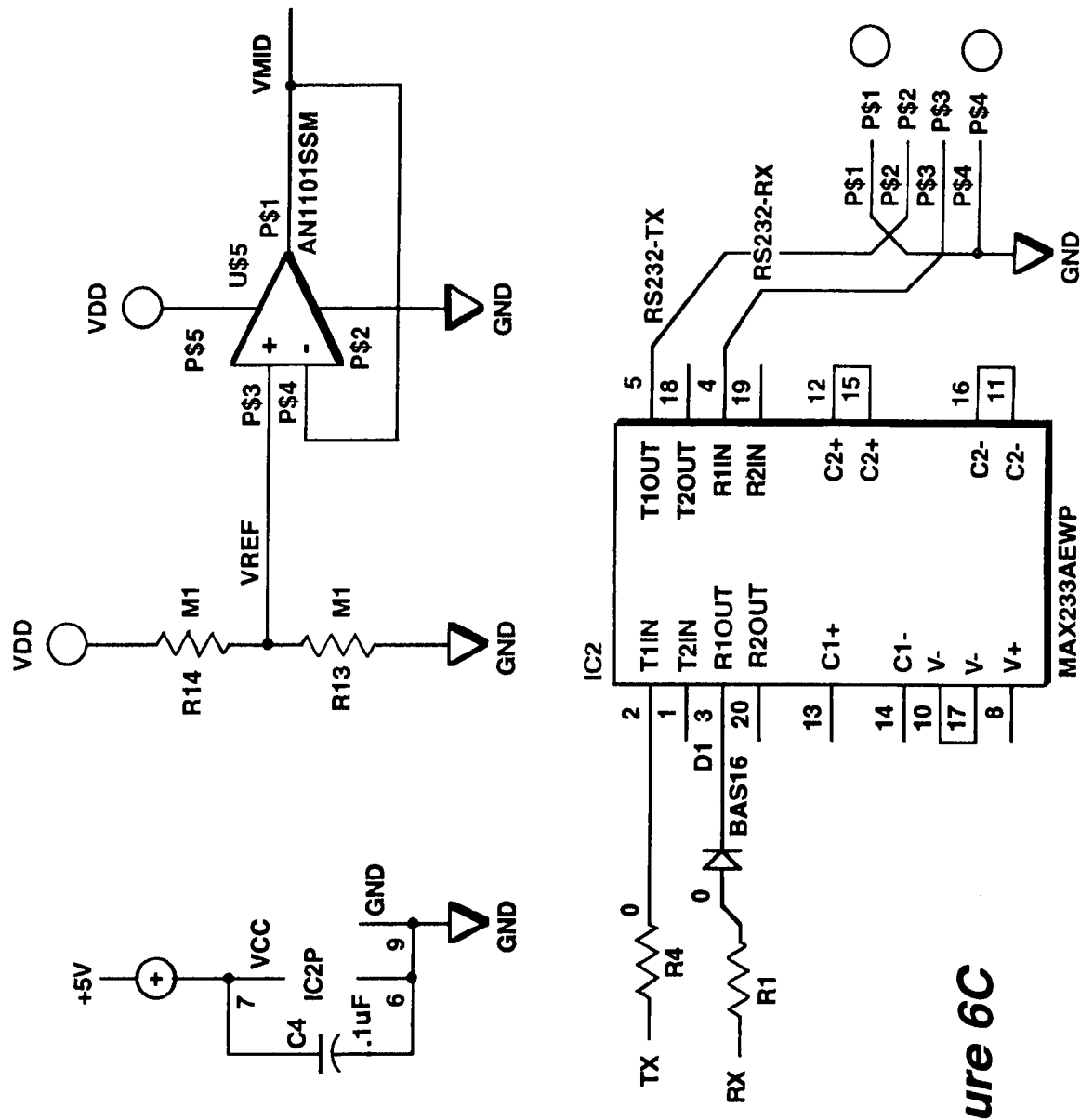
FIG. 6C is a schematic diagram of a third portion of the first hub according to principles of the invention.
Figure 6D:
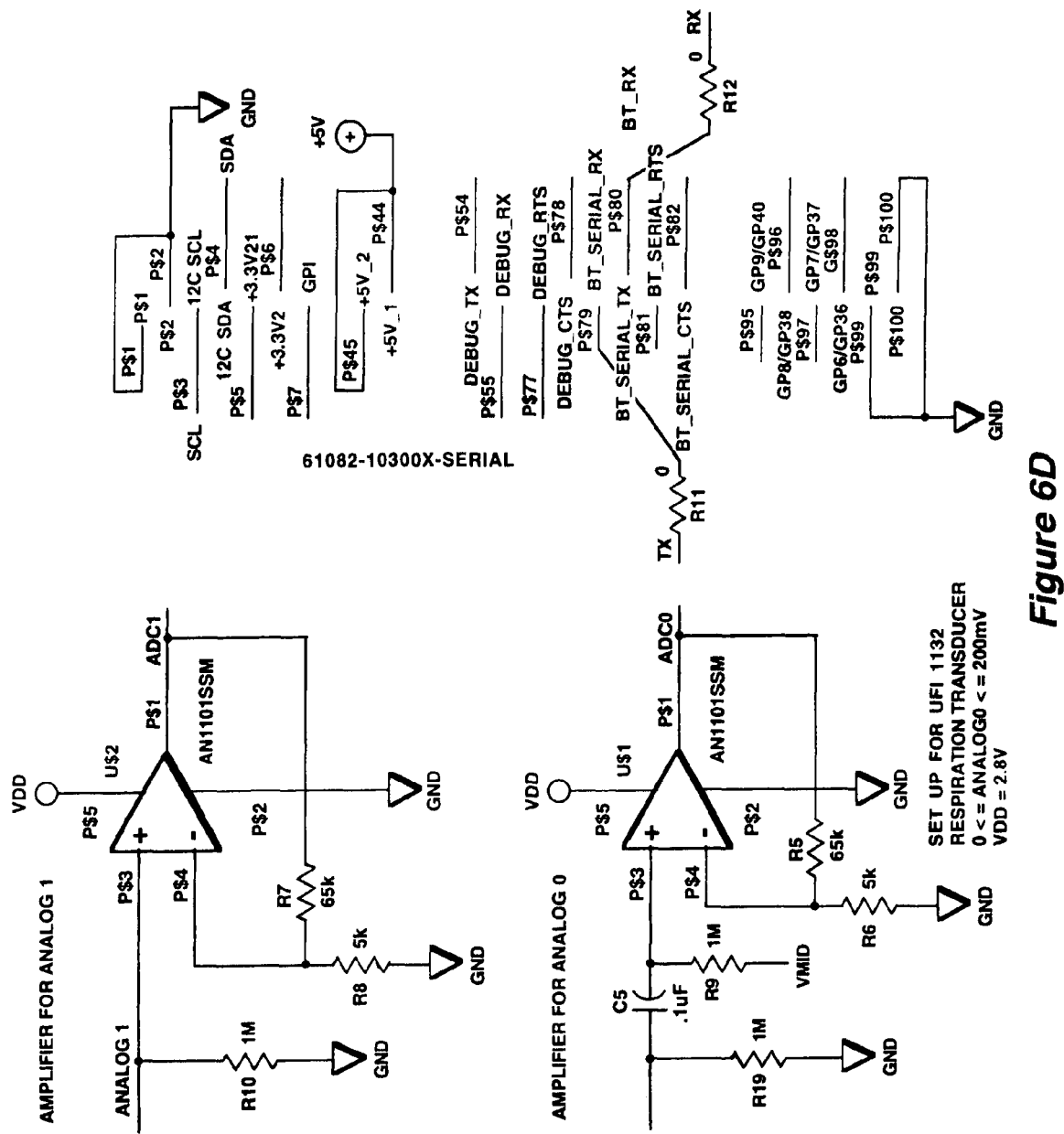
FIG. 6D is a schematic diagram of a fourth portion of the first hub according to principles of the invention.

FIG. 6A, FIG. 6B, FIG. 6C and FIG. 6D together are a schematic diagram of a first sensor hub according to principles of the invention. FIG. 6A shows a first part of the first sensor hub, FIG. 6B shows a second part of the first sensor hub, FIG. 6C shows a third part of the first sensor hub and FIG. 6D shows a fourth part of the first sensor hub. The core of the sensor hub module in the preferred embodiment is an Atmel ATMega-8L micro-controller of Atmel Corporation of San Jose, Calif. The micro-controller is connected to two unbuffered analog inputs, two buffered analog inputs, two digital input/outputs, RS232, I2C, and two Analog Devices ADXL202E 2-axis accelerometers. One accelerometer is mounted flat on the sensor hub board, and the other is mounted perpendicular on a daughter board. This configuration allows for the detection of 3-axis acceleration.

The buffered analog inputs are composed of one AN1101SSM op-amp for each input. One of these op-amps is configured as a ground referenced DC amplifier, and the other is configured as a 1.65 Volt referenced AC amplifier. A third AN1101SSM provides a stable output for the 1.65 Volt reference.

The RS232 is routed to either the Cerfboard connector or to the Maxim MAX233AEWP RS232 line level shifter. This allows the sensor hub to be connected to the Cerfboard through the logic level serial or to other devices through RS232 level serial. The I2C bus is also routed through the Cerfboard connector to allow for alternative protocols to be used between the sensor hub and the Cerfboard.

All the devices except the RS232 line level shifter use the 3.3 Volt power rail. The line level shifter uses the 5 Volt power rail, and the 5 Volt power rail is also routed to the Cerfboard through its connector.

Power Module

The power module is composed of a Linear Technology LTC1143 dual voltage regulator, a Linear Technology LT1510-5 battery charger, and related passive components for both devices. The LTC1143 provides a switching regulated 3.3 Volt output and a 5.0 Volt output for input voltages that vary from 6 Volts to 8.4 Volts when running from the battery or 12 Volts to 15 Volts when running off an external power supply. The LT1510-5 charges a 2-cell Li-Poly battery using a constant I-V curve at 1 Amp when a 12 Volt to 15 Volt external power supply is used.

Life Signs Telemonitor Low-Power 2.4 GHz

Figure 7A:
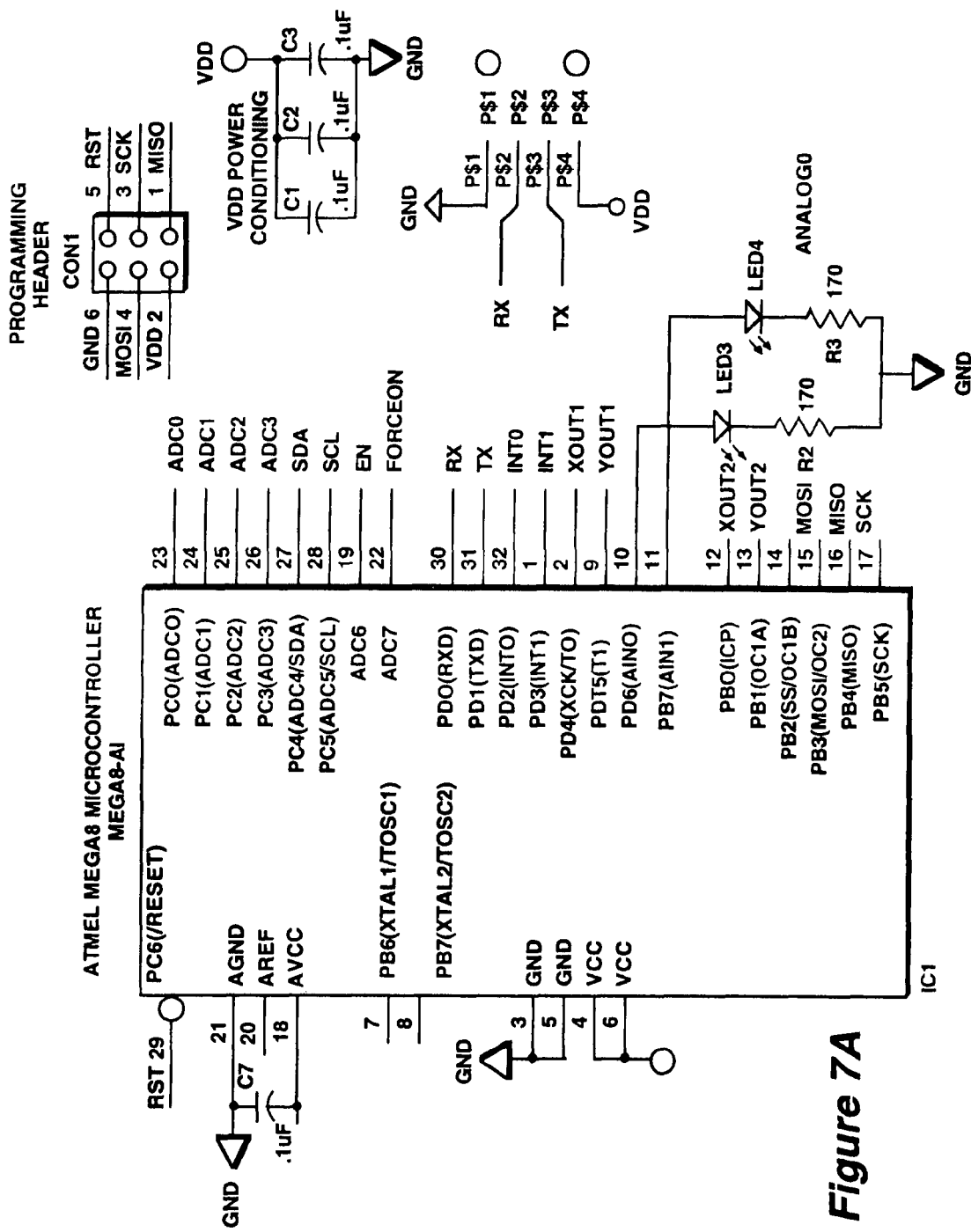
FIG. 7A is a schematic diagram of a first portion of a second hub according to principles of the invention.
Figure 7B:
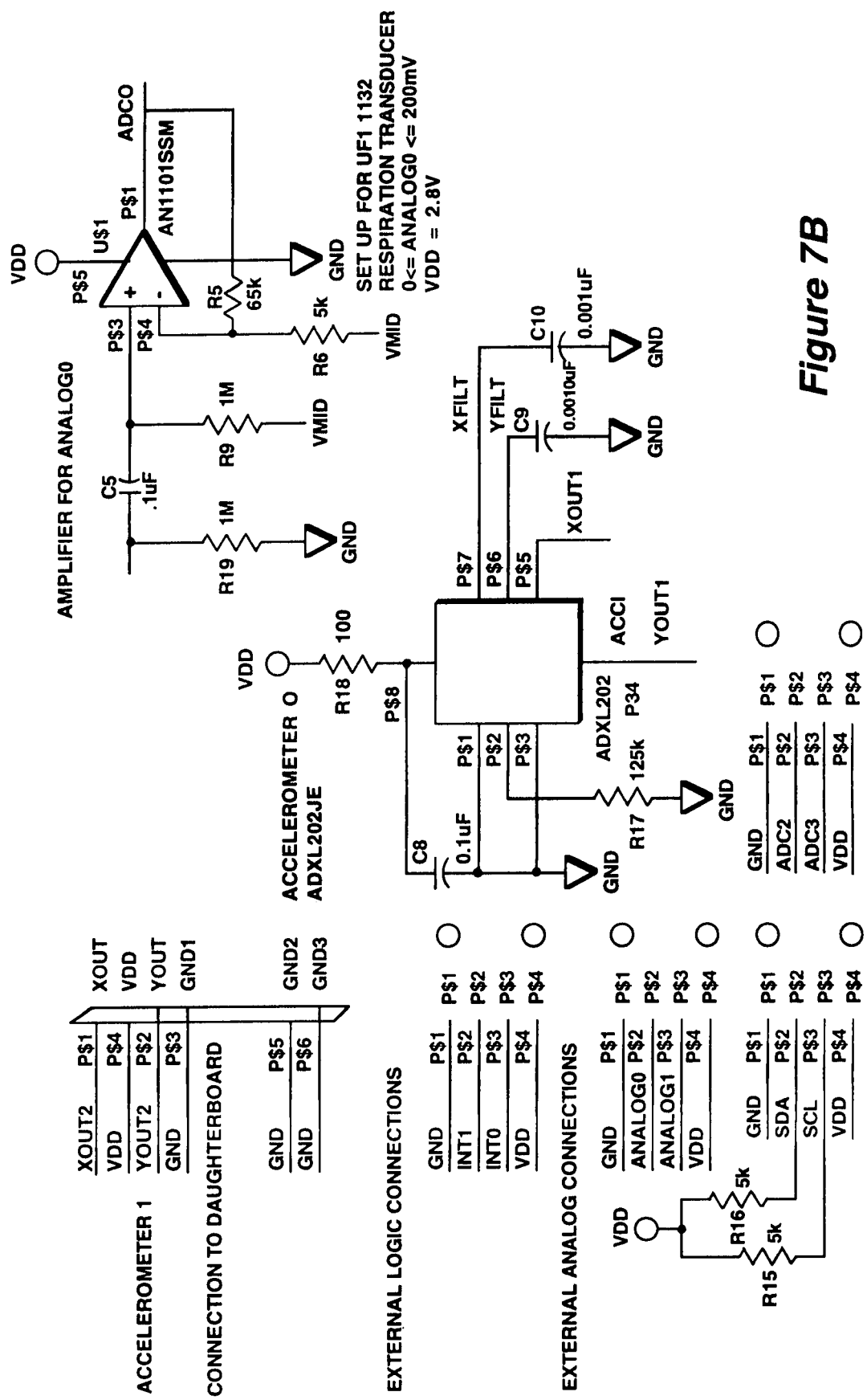
FIG. 7B is a schematic diagram of a second portion of the second hub according to principles of the invention.
Figure 7C:
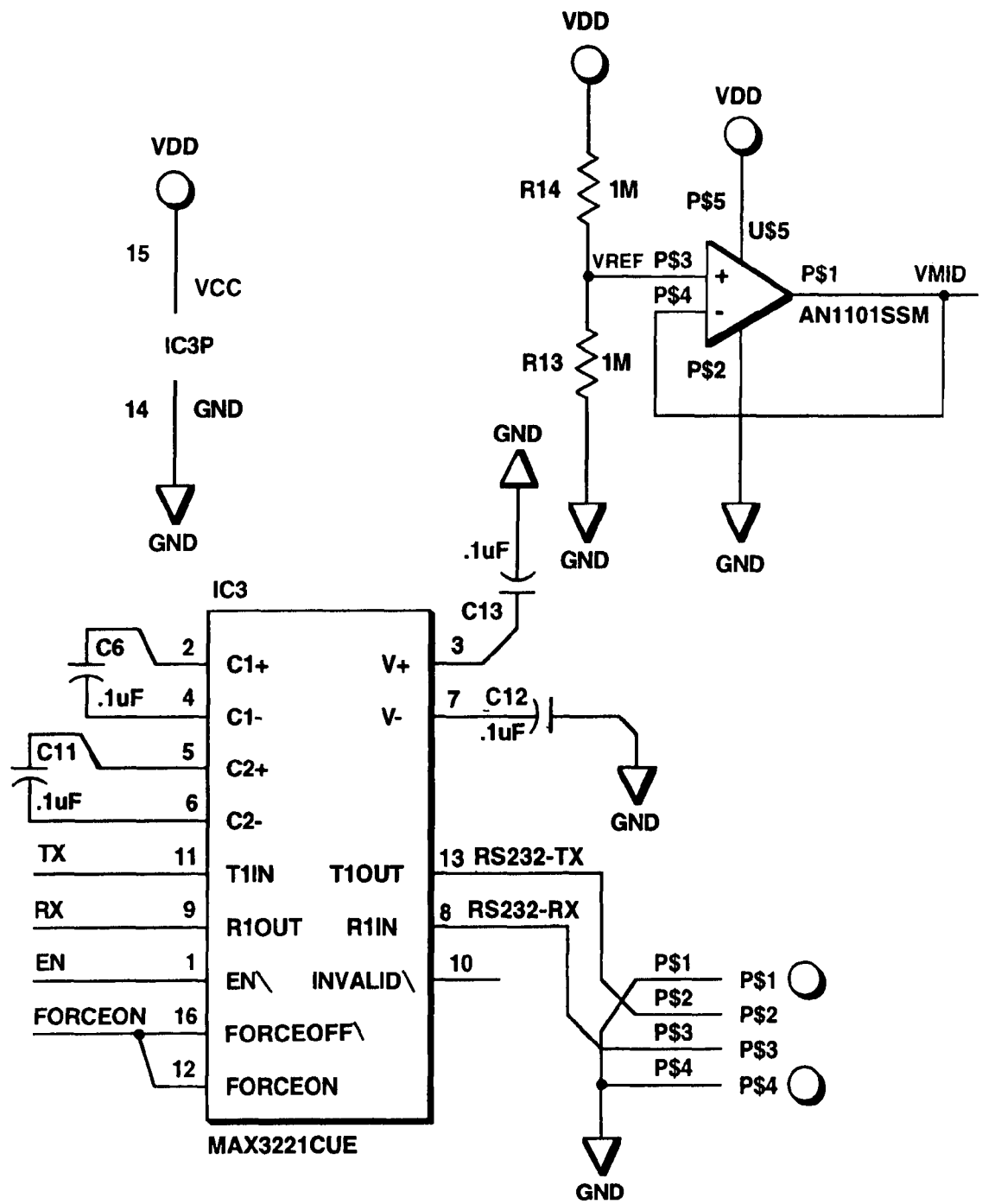
FIG. 7C is a schematic diagram of a third portion of the second hub according to principles of the invention.
Figure 7D:
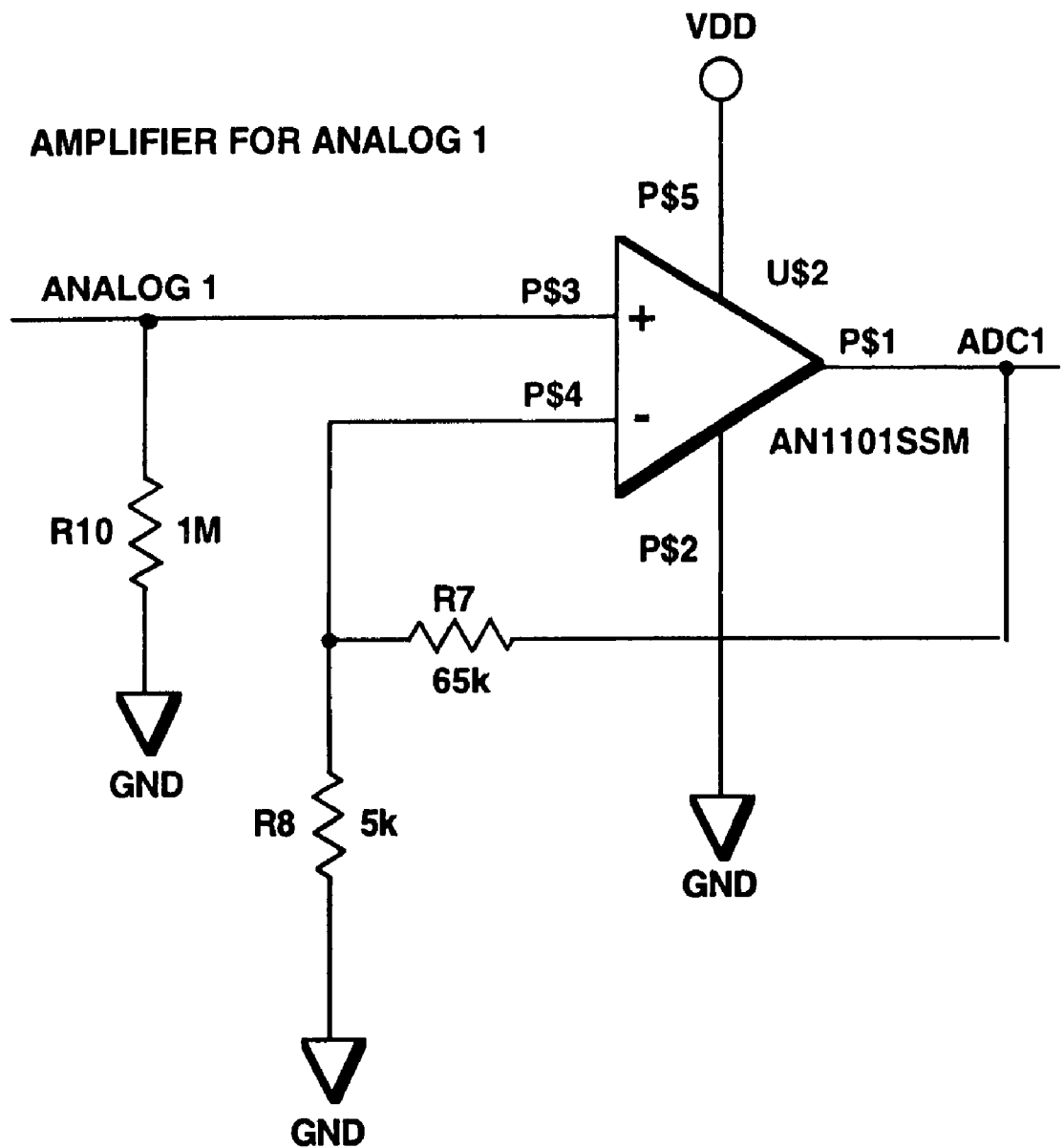
FIG. 7D is a schematic diagram of a fourth portion of the second hub according to principles of the invention.

FIG. 7A, FIG. 7B, FIG. 7C and FIG. 7D together are a schematic diagram of a second sensor hub according to principles of the invention. FIG. 7A is a first portion of the hub, FIG. 7B is a second portion of the hub, FIG. 7C is a third portion of the hub and FIG. 7D is a fourth portion of the hub. This hub is designed to provide sensor information over a short range radio link. By using a simple short range radio, the protocol can be handled on a lower power microcontroller. This reduces the space and power requirements from the 802.11 embodiment by not requiring a single board computer. The low power telemonitor is a single unit of hardware constructed from three modules.

The first module provides the power regulation system which outputs a 3.3 Volt power rail. The module can also optionally support a 5.0 Volt power rail and battery charger. The modules can run off of a Li-Poly 2-cell battery or a 12 volt regulated power source. These power rails are capable of handling loads of up to 450 mA. A power rail also charges the battery when an external power source is supplied. Due to the lower power requirements of this system, this module takes up less area and has shorter components than those used on the 802.11 system.

The second module contains the sensor hub and is nearly identical to the 802.11 version in terms of functionality. The difference is that the low power version provides its data via I2C to the third module instead of via RS232 to the Cerfboard.

The third module contains the low power, short-range radio system. This module takes the sensor data from the sensor hub module over I2C and transmits it over a short range 2.4 GHz radio link. The module may also be configured as a receiver for the sensor data transmissions, transferring the data to the destination data collection system over RS232 or I2C.

Sensor Hub Module

The core of the sensor hub module is an Atmel ATMega-8L micro-controller. The micro-controller is connected to two unbuffered analog inputs, two buffered analog inputs, two digital input/outputs, RS232, I2C, and two Analog Devices ADXL202E 2-axis accelerometers. One accelerometer is mounted flat on the sensor hub board, and the other is mounted perpendicular on a daughter board. This configuration allows for the detection of 3-axis acceleration.

The buffered analog inputs are composed of one AN1101SSM op-amp for each input. One of these op-amps is configured as a ground referenced DC amplifier, and the other is configured as a 1.65 Volt referenced AC amplifier. A third AN1101SSM provides a stable output for the 1.65 Volt reference.

The RS232 is routed to both a logic level connector or to the TI MAX3221 CUE RS232 line level shifter. This allows the sensor hub to be connected to other devices through the logic level serial or RS232 level serial. The I2C bus is connected to the adjacent modules to handle the routing of sensor data between modules.

Radio Module

The radio module is composed of an Atmel ATMega-8L micro-controller and a Nordic VLSI nRF2401 2.4 GHz transceiver. The nRF2401 provides a 2.4 Ghz 1 Mbit short range wireless RF link. The micro-controller configures and handles all communications between the nRF2401 and the rest of the system.

The micro-controller has an I2C connection to the adjacent modules to allow it to transport sensor data to and from other modules on the system. It also connects to a TI MAX3221 CUE RS232 line level shifter to allow the radio module to operate as a radio transceiver for an external device such as a laptop or PDA.

These modules contains all the needed passive components for the nRF2401 to operate in 1 Mbit mode including a PCB etched quarter wave antenna.

Power Module

The power modules contains 2 Maxim MAX750A switching power regulators, a Linear Technology LT1510-5 switching battery charger, and related passive components for each device. One MAX750A is configured to output a 3.3 Volt power rail, and the other is configured to output a 5.0 Volt power rail. Each of these rails is limited to 450 mA of current load. The input voltages to these regulators vary from 6 Volts to 8.4 Volts when running from the battery or is 12 Volts when running from an external regulated power supply. The LT1510-5 charges a 2-cell Li-Poly battery using a constant I-V curve at 1 Amp when a 12 Volt regulated external power supply is used.

FFT and Classifier Module

The Fast Fourier Transform ("FFT") software is programmed in machine language on the Atmel processor. Because the Atmel computational capabilities are limited, the volume of data to be transformed substantially in real time is considerable, the FFT algorithm needs to run fast. An algorithm using floating point is not generally compatible with present Atmel technology because floating point algorithms run too slow. Transforming the algorithm into fixed point made it possible for the algorithm to run with sufficient speed and with acceptable use of microcontroller resources.

Sensor information is input to the FFT algorithm, which computes the Fourier Transform as output. Such transformation of the original data into the frequency domain aids data analysis particularly in cases in which the phenomena are fundamentally oscillatory. Examples of such oscillatory data are ambulatory motion, heart beat, breathing, and motion on a vehicle that is traveling. This output is then input to a Classifier module, which analyzes and recognizes the pattern or patterns inherent in the data and compares them to patterns it has been trained to recognize using a statistical algorithm. The Classifier module output consists of one or more matched patterns along with the confidence level for the match.

Figure 9:
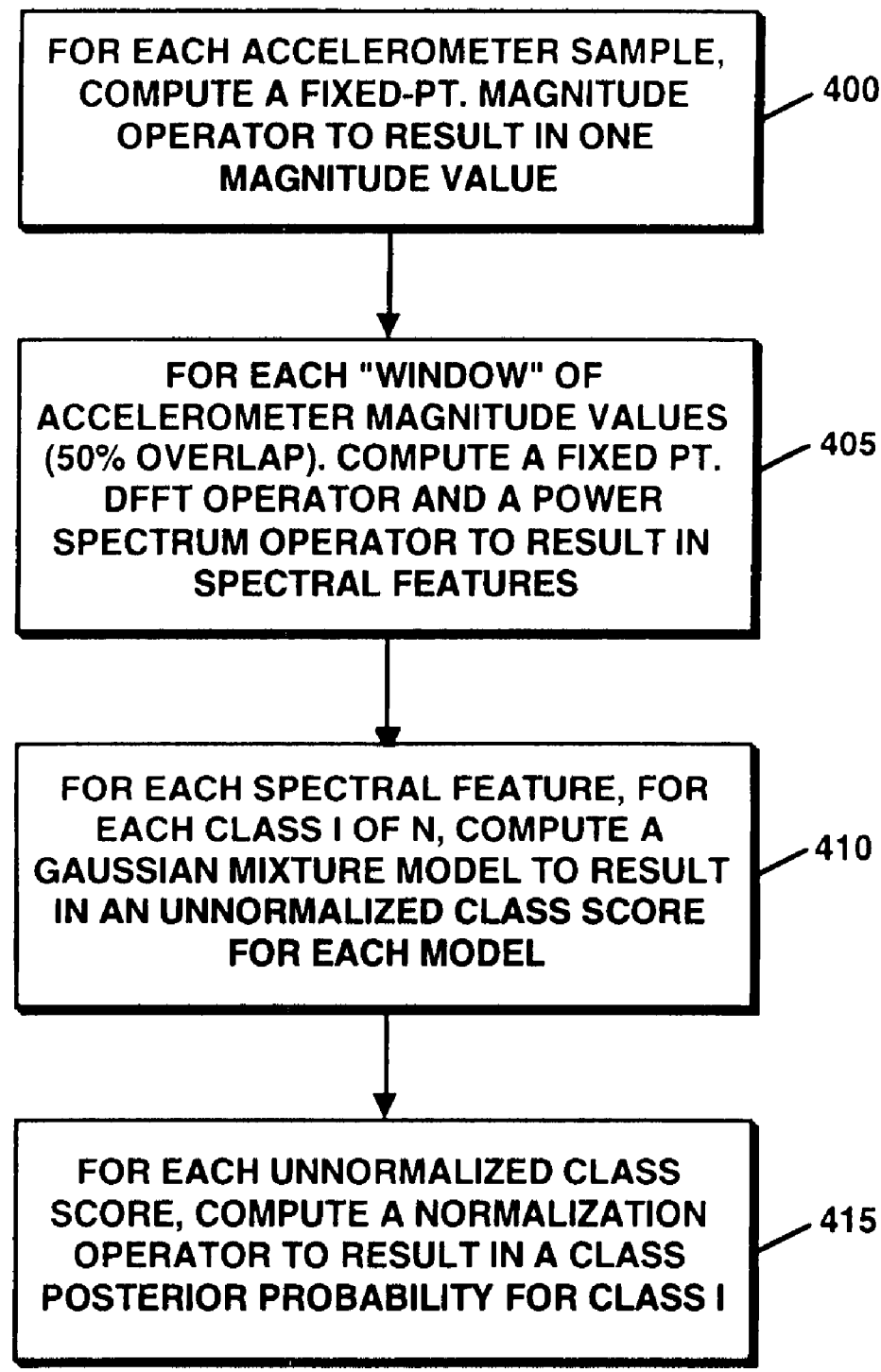
FIG. 9 is a flow chart of the process of the classifier module according to one embodiment of the invention.

FIG. 9 is a flow chart of the process of the Classifier module. At step 400, the Classifier module executes the following:

For each accelerometer sample, do:

three axis accelerometer sample ⟶

{fixed-point magnitude operator} ⟶ one magnitude value

At step 405, the Classifier module executes the following:

For each "window" of, for example, 64 accelerometer magnitude values (50% overlap), do:

64 magnitude values ⟶ {fixed point DFFT operator} ⟶

{power spectrum (mag square) operator} ⟶ thirty one spectral features.

Sample numbers are typically any power of two. If a larger number of values is used, more memory is generally required.

At step 410, the Classifier module executes the following:

For each vector of 31 spectral features, do:
    for each class (Gaussian mixture model) i of n, do:

31 spectral features ⟶ {Gaussian mixture model i} ⟶

$s_i$ (class score for model i)

Result is n unnormalized class scores.

At step 415, the Classifier module executes the following:

For each unnormalized $s_i$, do:

$$s_i \longrightarrow \{\text{normalization operator}\} \longrightarrow p_i \text{ (class posterior probability for class i)}$$

Result is class posterior probabilities for each class, given the window of 31 spectral features.

The display of the output information in the presently preferred embodiment is a listing of patterns matched along with confidence levels. Those skilled in the art will recognize that many alternative displays can be useful. Examples of such displays include a red-yellow-green light for each of one or more matches, and a color coded thermometer with the color representing an action to be taken and the height of the indicator a measure of the confidence with which the Classifier determined this to derive from a correct data-model match.

The manner in which the information is visualized is supportive of the core feature of "alarming" based on the output of the classifier. The core feature of the "proactive telemonitor" is that it is proactive. In some embodiments of the invention, nothing is displayed until the health state classifier (or environmental conditions classifier, the injury classifier, etc.) detects that there is a problem, and calls for help. This implementation is feasible because it utilizes principled classification to drive proactive communications and user interaction rather than merely displaying information or sending an alarm upon the overly simplistic criterion of some data parameter being exceeded.

In alternative embodiments of the present invention, other types of microcontrollers other than the Atmel microprocessor may be used. Many low complexity, basic microprocessors are suitable for use in the present invention. The present invention is not limited to the microprocessors listed here.

Low Power State Classification

State classification refers to the process of automatically and systematically inferring aspects about the state of a system (e.g. a person, a vehicle, etc.) through the analysis of sensor data. State classification can provide value to a wide range of applications, from athletics and sports performance enhancement, to metabolic modeling, to the detection of incipient mechanical failure in complex mechanisms, to neurological condition diagnosis, to the detection of drug side effects, incipient disease, or falls or other dangerous conditions. In order to make state classification practical for a given application, the following application-specific criteria are preferably met:

1. Sufficient accuracy (typically expressed in terms of a false positive vs. false negative rate for each class, or overall percentage accuracy) and reliability. For most applications, sufficient accuracy is generally an overall percentage accuracy between 85% and 97%, with a false positive rate between 3% and 15% and a false negative rate below 1%.
2. Sufficiently low latency of the classification process. For most applications, sufficiently low classification latency is typically between 30 seconds and five minutes.
3. The classification system includes sensing, signal processing, communications, and computing elements, to be implemented within engineering and usability constraints. These constraints include, but are not limited to:

Physical packaging and human factors considerations, including overall size and weight. For example, a body-worn classification application might impose a volume constraint of one cubic inch and a weight constraint of one ounce, including sensors, batteries, packaging, and wireless communications or interaction elements.

The system will operate within the constraints of a power budget. For body-worn applications, this translates to operating for a sufficiently long period of time without recharging or otherwise replenishing a body-worn stored power source. This run-time constraint may range from requiring days to months of continuous operation, depending on the application.
4. The classification system includes cost constraints. Cost factors include the expense of designing and running an appropriate data-acquisition study and the costs of data analysis and classifier development. Cost factors further include the costs of engineering the deployed classification system, which may include electronic, mechanical, human factors, and software/firmware engineering costs, the cost of producing the deployed classification system (cost of parts, fabrication, assembly, and quality assurance/quality control), and testing/evaluation costs. It is worth noting that for a given design process, the engineering costs are relatively fixed (do not vary with the number of units produced) but the production costs scale with the size of the production run, and in large unit numbers ultimately dominate the engineering costs. By using the process taught here, it will be possible to significantly reduce the cost of the parts, allowing for complete classifications systems to be manufactured for costs below $30 per unit.

The applicability of a state classification process is maximized in situations involving high-accuracy, low latency, light-weight, little power consumption, and a need for a system that is inexpensive to implement. Those who are skilled in the art will recognize that there are inherent trade-off among these criteria—e.g. it is often possible to lower the latency of a classification process if one is willing to use more expensive and power-hungry signal processing and computing hardware. Likewise, for battery powered systems, the use of a smaller battery may be traded off against the need for more frequent replacement or recharging, etc. Unless the number of units to be fabricated is large, the costs of developing the classification implementation may dominate the costs of actually deploying the system.

Embodiments of the present invention include a method of implementing a classification system which trades off increased time and effort in design for large gains in efficiency, accuracy, power reduction, and cost reduction in implementation. Embodiments of the present invention further include a method of implementing state classification that combines light-weight, low-power sensors with light-weight computational resources and specific computational techniques that allow the computational requirements in storage (RAM) and computing power (MIPS) to be reduced by between, for example, two and three orders of magnitude compared to more conventional implementations. As a result, small, light-weight, and inexpensive implementations are possible, which significantly broadens the sphere of applicability of state classification, and enables many applications which would otherwise have been cost-prohibitive.

State Classification Process

The state classification is defined as an automatic process of real-time measurement, analysis, and interpretation that results in useful knowledge or conclusions about the state of the measured system. For example, it is often important to know whether a fuel tank is running low so that the operator of a system may be notified. This determination is made in real-time (frequently, and with low latency) so that the operator can be notified in a timely fashion. This application has two parts: (1) fuel tank state classification (two states, "running low" and "not running low") and (2) operator notification. To make this classification process feasible, two things are needed: (A) some feasible means of accurately measuring fuel level in real-time, and (B) a definition of the classes "running low" and "not running low" so that a classification system may be designed that can measure the fuel level and make this determination.

Simple classification problems, such as the example described above, are well known in mechanical engineering and systems control theory, and generally need only ordinary skill in the art of measurement systems design, control theory, and related disciplines to address adequately. There are, however, many state classification problems that pose greater challenges, either because the phenomenon of interest is not easily directly measured, or because the phenomenon is complex enough that measurement calls for more sophisticated interpretation. It is the latter class of state classification problems that the methods taught in this disclosure are primarily designed to address. Regardless of the complexity of the problem, the foundation process of real-time measurement and measurement interpretation remains the same.

For the category of more difficult state classification problems, the classification method typically involves the following five steps:

1. A transducer or transducers (sensors) measure a time-varying physical property of some system or systems in the real world. For example, the transducer may be an inexpensive MEMS accelerometer with an analog or digital output. The result of the measurement is a continuous, time-varying transducer output signal 1.

2. This transducer output signal is amplified and filtered to produce a sensor signal that is appropriately amplified and band-limited for digital sampling. The dynamic range and output impedance of the amplification and filtering stage is engineered to match the input requirements of the digital sampling hardware. Some transducers will produce multiple output signals, such as multi-axis accelerometer. Transducers (and associated electronics) that produce more than one signal are called multi-channel sources.

3. A microcontroller or other type of processor digitally samples the sensor signal (or signals, in the case of a multi-channel source) at a predefined sampling rate. If the transducer produces an analog signal, sampling involves analog to digital conversion (ADC). If the transducer is digital, it may produce a pulse width modulation (PWM) signal or implement a higher-level digital protocol interface, such as the Phillips i2c protocol. The result of digital sampling is a signal of "raw" digital sampled values. The properties of this digital signal are characterized by the number of bits per sample, the number of channels sampled, and the sampling rate.

4. Additional digital signal processing (DSP) operations may be performed on the signal after sampling in order to transform the signal into a form suitable for classification. This step is called feature computation. For state classification, feature computation typically involves analysis of the signal's dynamic behavior, or how the signal changes over time. Usually this involves examining a time-bounded set of samples together, also called "windowing." Windowing may be used to compute signal time derivatives, or to perform more complex analysis, such as Fourier or spectral analysis based on the short-time-windowed discrete fast Fourier transformation (DFFT) algorithm. One skilled in the art will understand that many other types of feature computation and signal dynamics analysis are possible, including integration, FIR filtering, IIR filtering, thresholding or peak detection, matched filters, etc. The result of the feature computation step is a digital signal of (possibly multi-dimensional) computed features. In some cases multiple feature computation stages may be used, with the input of successive stages being the output of previous feature computation stages.

5. Model evaluation. In the model evaluation process, one or more elements of the feature signal are evaluated by a previously chosen set of discriminative or generative models. The results of this evaluation are one or more class posterior probabilities (the probability of a given state or class given the evidence), or in the case of discriminative modeling, the single most likely classified state.

This abstract five-stage process is illustrated in the context of the following concrete example. The example state classification system is designed to classify soldier physical activity for metabolic modeling applications. All digital sampling and computation for this example system is implemented on Atmel ATMega8 microcontroller, generally a low-cost general-purpose embedded computing device. This example system is designed to distinguish between a low or resting activity state, a walking state, and a running state. Complicating this problem is that the "low" activity state corresponds not only to standing or resting, but also to riding in any of five specified military vehicles, including a tank, several troop transports, and a helicopter. In this example system, there are eight classes of interest, five vehicle classes and three non-vehicle classes. Since the vehicle classes and the "resting" class are equivalent from a metabolic load standpoint, if the maximum likelihood class is determined to be any of the five vehicles or the non-vehicle resting state, "low activity" is the reported state.

Sensing: A three-axis MEMS accelerometer (the ADXL330 produced by Analog Devices) is mounted on the torso and measures body acceleration over a ±3 G range.

Sampling: Three filtered analog sensor outputs, each corresponding to one axis of acceleration, are digitally sampled 50 times a second with 8 bits of resolution per axis. The result is a digital signal of 24-bit acceleration vectors, with 8 bits of precision per axis.

Feature Computation: For each sample vector, the magnitude is computed, resulting in a new acceleration magnitude signal. For each "window" of 64 magnitude values, a short-time-windowed DFFT is computed, resulting in a new feature signal composed of 64-dimensional vectors of complex-valued frequency components. For each 64-dimensional DFFT vector, the power spectrum is computed, resulting in a new feature signal of 32-dimensional power spectrum vectors. For each 32-dimensional power spectrum vector, a six-dimensional real-valued factor vector is computed as the product, where M is a 6×32 factor weight matrix. The result is a new feature signal of 6-dimensional real-valued factor vectors.

Classification: For each 6-dimensional factor vector, the class posteriors for seven internal activity classes are computed, where each of the seven internal classes is represented by a single homoschedastic 6-dimensional Gaussian model. (Class posteriors are computed according to Bayes' Rule, as discussed below.) The result is a seven-dimensional normalized class posterior vector. The result is a "first-stage" class posterior signal, which acts as a new feature vector for the second-stage classifier. For each seven-dimensional first-stage class posterior vector, the maximum value (highest class posterior) index is determined, resulting in a new feature signal of maximum likelihood class indexes. The second stage classifier is a collection of eight first order Markov models (MMs), which capture first-order state-transition probabilities between the maximum-likelihood class indexes computed in the previous step. The MMs are evaluated on the last eight indexes, and the second stage class posteriors are computed using Bayes' Rule. The result is a normalized eight-dimensional second stage class posterior vector, with the probabilities for each of the eight activity classes (five vehicular activity states, three non-vehicular states).

Due to the complexity of the process, it might appear unlikely to those skilled in the art that the classification system described above could be implemented using an 8-MIPS microcontroller with 1 k of RAM. Using the techniques described in this disclosure, however, it was not only possible to implement this system with high accuracy (97% accurate for metabolic load classification) but to do so using much less than 1% of the ATMega8's CPU cycles.

In the discussion that follows, a specific set of development and implementation techniques for engineering real-time state classification systems is described, including classification of health state using a range of simple physiological sensors, the classification of events such as ballistic impact, vehicle crash, or nearby explosions using acoustic sensors, the classification (authentication) of user identity based on device usage and motion patterns, etc.

Signal Filtering, Sampling Rate, and Sampling Precision

In this section, the closely related topics of sensor signal band limitation, filtering, and sampling are described. Taken together the techniques described here represent an approach to limiting the bandwidth of the sensing and sampling system at each stage. Bandwidth management yields large benefits in the form of reduced power consumption and reduced subsequent data storage and computation.

Matching a sensor or measurement system to a classification application involves choosing a sensor that provides sufficient salient information so that the classification task may be accomplished with the specified latency and confidence requirements. Any real sensor has practical limits in dynamic range, frequency response and resolution. Useful sensors have well characterized dynamic range and accuracy limits over a specified operational frequency band. To be appropriate for a classification application, the operation band and resolution of a sensor generally correspond to salient (in the sense of providing useful information for classification) features of the system being measured.

A measurement system can fail in many ways, but there are two important failure modes to consider when setting band and resolution limits: failure to capture enough salient information, and the capturing of too much information, or too much information of the wrong type in proportion to the salient information that is also being captured. Of these two types of failures, the most common by far in the design of classification systems is the latter. In particular, it is frequently assumed by classification system designers that in order to achieve the desired level of accuracy, sensor signals must be sampled at the highest support rate and with the highest meaningful precision. While this type of maximalist filtering and sampling might be appropriate for a preliminary characterization of the signal prior to the engineering of the classification system, such an approach is almost always counterproductive if tight size, weight, power consumption, and cost limitations are to be met.

Filtering

Filtering is the process by which some part of an input signal is preferentially amplified in or excluded from an output signal. The term "filtering" refers herein to analog filtering of a sensor output in order to place an effective upper-bound on the frequency content of a sensor signal. There are many ways to do filtering, depending on the nature of the signals involved.

Most analog sensors produce a variable current or voltage output. To be used in a digital signal processing system, the sensor output signal is converted to a low-impedance variable voltage signal that is shifted and scaled as necessary to fall between zero volts and the maximum input voltage of the analog-to-digital converter, or ADC. The appropriate method of shifting and scaling the signal to produce a low-impedance, full-range signal depends on the nature of the sensor output. Designing the analog electronics to accomplish this shifting and scaling is a conventional analog electronics design problem which can be addressed by one of ordinary skill in the art.

Either after or during the shifting and scaling process but before sampling, the signal is appropriately band-limited for the sampling rate of the ADC. Those skilled in the art will recognize that there are many ways of implementing band-limiting filters, and that the best choice depends on a number of implementation-specific factors.

Figure 10:
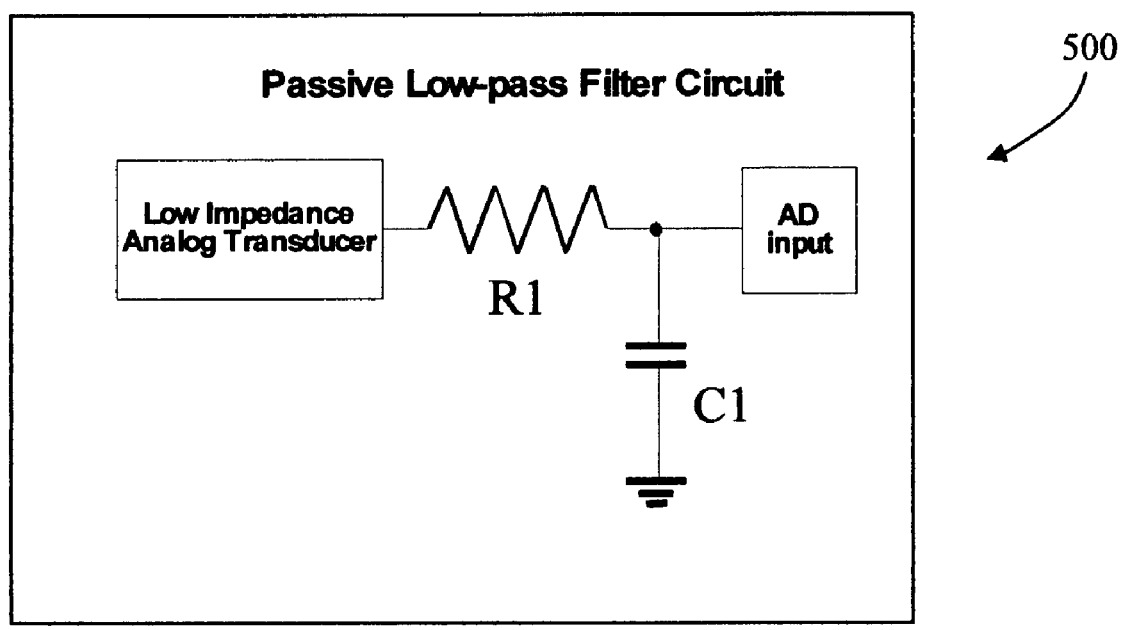
FIG. 10 is a block diagram of a filter suitable for use in embodiments of the present invention.

FIG. 10 shows a basic band-limiting filter 500, the passive low-pass filter. In a passive low-pass filter, the f3 db point—the frequency at which 3 db of attenuation will occur—is calculated as $1/(R1 \cdot C1)$. More complex filters (such as active op-amp based combined amplifiers and filters) are also characterized by the f3 db point, though the method of calculating this point is different for other filter types. Regardless of the type of filter chosen, the filter is generally designed so that the f3 db point is just above the highest frequency of interest in the sensor signal. Even when the highest frequency of interest is the highest frequency the sensor can produce, it is still necessary to band-limit the signal before sampling in order to filter out extraneous high-frequency noise that is present in mixed signal (combined analog and digital) systems. In such cases, the filter is designed so that its f3 db point is just above the sensor's f3 db point.

In many cases, the highest frequency of interest is lower (sometimes far lower) than the maximum useful frequency produced by the sensor. In such cases, the filter is designed with a lower f3 db point so that a lower ADC sampling rate can be used.

ADC Sampling Rate Selection

The choice of filter f3 db dictates the minimum ADC sampling rate needed. One of the most important results of information theory is that given a band-limited continuous signal, such a signal can be perfectly reconstructed from a set of real-valued (infinite precision) measurements or samples (the value of the signal measured at a particular time t) taken at regular intervals, provided that the sampling rate fs is greater than twice the highest frequency in the original signal, i.e. $fs > 2 \times f3\ db$ This is known as the sampling theorem, and provides the foundation for the digital recording of music, images, and all other digital representations of continuous signals.

While in theory any frequency fs chosen such that $fs > 2 \times f3\ db$ will work, it is important to chose a sampling frequency that is as low as practical so that the benefits in reduced signal bandwidth achieved by aggressive band limiting are not lost. A practical range is $fs = a \times f3\ db$, $4 \geq a > 2$. Those skilled in the art will understand that analog filtering does not produce a "hard" cutoff at the f3 db point, and that a choice of alpha well above 2 but less than 4 will minimize the likelihood of signal aliasing resulting from the occasional high-amplitude, high-frequency component in the sensor signal.

ADC Sampling Resolution Selection

Digital samples do not have infinite precision, but instead have a finite resolution that is determined by the number of bits per sample, e.g. an 8-bit digital sample uses eight bits, which can take on 256 distinct states. In order for an 8-bit number to represent the value of a sample, there is a mapping for every possible value of the signal to one of the 256 possible states. For example, the input signal to an 8-bit ADC might be a voltage that varies continuously between 0 and 3.3 volts. The digital sampling process maps the real-valued domain $0 \leq x \leq 3.3$ to a range of 256 discrete states, which can be interpreted as corresponding to the integers between 0 and 255, inclusive: ADC $(x) \in \{0, 1, 2, \ldots, 255\}$.

Signals may be continuous, but sensor signal typically have finite resolution, meaning that changes in signal value smaller than some delta are generally meaningless. The full resolution of a signal, however, is seldom required to achieve acceptable accuracy in a classification task. When implementing a classification system according to the method taught here, the designer ideally selects the lowest possible sampling resolution that supports the desired classification accuracy, not (as is often the case) the highest supported by the precision of the sensor signal. In some cases sensor signals that would support 16 or 24 bits of precision may be sampled with as little as 8 or 2 bits of precision with no loss of classification accuracy.

If the resolution of the ADC is too low, the lost information may create classification accuracy problems. If the resolution too large, more storage and processing power will be required to deal with the signal than is necessary. Choosing an appropriate ADC resolution—one that provides sufficient accuracy without undue overhead—is a consideration in designing a real-time classification system. By choosing the practical minimum number of bits of precision necessary for the signal processing and classification application, the actual amount of data that is stored and processed is limited, which is important for reducing the computational power requirements (and hence cost, complexity, and power consumption) of the embedded processor.

Another important reason to choose the practical minimum sampling resolution is that the ADC process is expensive in terms of power consumption. ADC power consumption scales with ADC accuracy, so an important part of the present art is the direct power-management benefits that result from choosing the lowest practical number of bits of precision.

Digital Processing Techniques for Real-Time Classification

Subsequent to ADC, all operations are performed by digital computing resources, typically a microcontroller or other embedded processor. Implementing these operations so that they require a minimal, fixed amount of computing resources is critical to successful implementation using light-weight, embedded computing resources.

Creating an efficient implementation is not generally sufficient. If the resources required for performing any of the required operations is variable, it can be difficult to characterize the true maximum resource requirements for the system. For this reason it is necessary to implement each step so that the step takes a fixed amount of time regardless of the inputs. Fixed-time operations allow for reliable scheduling in the absence of a real-time operating system or other high-level, heavy-weight resource management system.

Now described are three important techniques for implementing the digital processing steps of a real-time classification system: constant-time fixed point arithmetic, constant-time natural log probability arithmetic, and homoschedastic representation of normal distributions.

Constant-Time Fixed Point Arithmetic

Fixed-point arithmetic is the use of integer numbers to represent fractional values with an implied radix or decimal point.

Two fixed-point binary representations- the
  first is a conventional eight-bit integer number,
the second is an eight-bit fixed point number
  with the radix three digits from the right.
In both cases, the binary digits(bits) are
  represented by the subscripted symbols $b_1 \ldots b_8$.

$$b_8 \cdot 2^7 + b_7 \cdot 2^6 + b_6 \cdot 2^5 + b_5 \cdot 2^4 + b_4 \cdot 2^3 + b_3 \cdot 2^2 + b_2 \cdot 2^1 + b_1 \cdot 2^0$$

$$b_8 \cdot 2^4 + b_7 \cdot 2^3 + b_6 \cdot 2^2 + b_5 \cdot 2^1 + b_4 \cdot 2^0 + b_3 \cdot 2^{(-1)} + b_2 \cdot 2^{(-2)} + b_1 \cdot 2^{(-3)}$$

(Integer arithmetic can equivalently be viewed as a special case of fixed point arithmetic in which the decimal point is to the right of all digits.) Constant-time fixed point arithmetic is a subset of fixed-point arithmetic operations implemented such that each operation takes a fixed amount of processing time, regardless of the inputs. In one embodiment of the invention, constant-time processing is achieved for all digital signal processing, feature computation, and model evaluation are implemented using constant-time fixed point arithmetic.

Floating point arithmetic (which is the conventional system for working with fractional numbers in modern scientific and technical computing) uses a more complicated representation in which the radix is allowed to move ("float") so that any number of digits (to within an overall precision limit) can be to the right or left of the radix. Furthermore, floating-point arithmetic routines allow operations on numbers with different radix positions. Floating point arithmetic is more general, since it allows very large and very small values to be represented with equivalent precision. The use of floating-point arithmetic, however, is significantly more expensive than fixed point arithmetic in terms of computational complexity and storage. Even with specialized hardware support provided by contemporary desktop and server processors, a well implemented fixed point calculation program typically outperforms an equivalent floating-point program on all but the very fastest of today's scientific computing and supercomputer hardware.

The advantage of using constant-time fixed point math in computation is threefold: First, operations in fixed point are implemented as integer math operations, which are vastly faster than floating-point operations on embedded microcontroller hardware. Second, representing fixed point numbers useful for signal processing and classification generally requires less storage (RAM) than the smallest useful single-precision floating point representation. The latter is an important consideration, since the amount of RAM provided by microcontrollers is proportionally even smaller than the amount of processing power they offer, compared to desktop/server hardware. Finally, constant-time fixed point arithmetic provides the feature that a computation will take a fixed amount of time regardless of the inputs, making it possible to construct feature computers and model evaluators that operate in fixed time.

There are disadvantages in using fixed-point representations. These disadvantages have significant implications not just for the implementation of real-time classification systems, but also for the design of these systems as well. Fixed point calculation is optimized for values within a specific, limited dynamic range and resolution, whereas a floating point implementation can operate over a much larger range and resolution. By way of contrast, a 16-bit fixed-point representation with eight bits to left and right of the radix can represent values between 0.0 and 255.996 with $\frac{1}{256}$ fractional resolution. The smallest standard floating point representation is IEEE single-precision, which requires 32 bits. IEEE single precision can represent numbers in the $\pm 10^{38.53}$ range, with a fractional resolution of 0.0000001 ($\frac{1}{2^{23}}$) for values in the $\pm 1$ range.

When working with fixed-point numbers, one chooses at the outset where the radix will be placed, and once chosen, this location cannot be changed. This means that for a given calculation, the programmer typically needs to know much more about the required range and resolution of values expected to write a useful fixed point implementation than to write an equivalent floating point implementation.

Effectively using fixed point involves a step-by-step analysis of the range and resolution of the data at each stage of the classification process, from the initial feature computations to the final representation of class posteriors. At different stages of the process it may be necessary to use different fixed-point representations, either in data size, radix position, or mode of interpretation—for example, when working with probabilities associated with generative classifiers, it may be most appropriate to use a fixed-point negative log representation. (Fixed-point negative log representation is discussed in more detail below).

Because fixed point representations are fundamentally "integer," standard integer arithmetic operations may be used to work with them. In many cases, standard integer math libraries are inappropriate because of the need to work with mixed representation types and size. Likewise, in many cases an analysis of the ranges of the fixed point values allow the implementation of higher-performance constant-time math routines by ignoring the possibility of register overflow, etc. For this reason it is often necessary or desirable to implement constant-time fixed-point calculation using specialized, hand-coded assembly math operations. In order to assure the accuracy and reliability of any fixed-point calculation it is necessary to test it side-by-side with a known-correct implementation, which will typically employ floating-point representations.

For many real-world state classification applications, no more range and resolution is necessary than that provided by a 16-bit fixed point representation if sufficient care is taken in the implementation. Engineering the signal processing and state classification system to operate in fixed point involves a more careful analysis of data range and resolution requirements up-front, but with the substantial payoff of significantly reduced storage requirements and vastly increased performance.

Constant Time Natural Log Probability Arithmetic

Probabilities, or normalized probabilities, are numbers between zero and one. Probabilities, unlike some other fixed-range values, can be quite small and can still be important in a state classification calculation. Indeed, for some types of generative classifiers (such as Hidden Markov Models) meaningful comparison between probabilities on the order of $1 \times 10^{-20}$ may be required, yet at the same time it is necessary to represent probabilities as large as 0.99. A floating-point representation would provide the d dynamic range and precision for at least some applications, but at a significant cost (as has been previously pointed out in the discussion of fixed-point math, above). Instead, a fixed-point log-representation with an implicit negative sign will allow for compact representation and easy multiplication. In this notation, a stored value of 0.0 corresponds to $2^{-0}$ power, or 1, and a stored value of 255.0 would correspond to a value of $2^{-255}$, or $1.73 \times 10^{-77}$. Any number of fixed point representations can be chosen, but a 16- or 32-bit value with eight bits to the right of the radix accommodates most applications.

In embodiments of the present invention, in implementing fixed-point arithmetic, all log probability arithmetic operations are implemented to execute in constant time regardless of inputs. While multiplication is easy in a log-representation (multiplication becomes addition) addition of probabilities may also necessary, especially for normalization. To implement addition in log space, it is necessary to note that in general, if $\log(a) > \log(b)$, then $\log(a+b) = \log(a) + E$, where $E \leq \log(2)$. For log base 2, this means that $\log(a) \leq \log(a+b) \leq \log(a)+1$. (For other log bases there is a similar small range.) For most cases, $\log(a+b)$ can be accurately approximated as $\log(a)$, and for the special cases where a and b are close enough in value to matter, good results can be obtained with a small lookup table indexed by the results of a–b. Due to the necessity of performing comparisons and resorting to a lookup table for addition, special care is required when implementing the addition operator to ensure constant time operation.

Although working with base-two logs may seem natural in a digital computing context, when working with probabilities it makes more sense to use the true natural, or base e log. This is because one often evaluates Gaussian or normal distributions, which are based on the exponential function, otherwise known as $e^x$. By staying in the natural log space, no exponentiation is required, saving computing cycles. For the purposes of this disclosure operations on probabilities are presumed to be performed using constant-time natural log probability arithmetic.

Working with Gaussian Distributions

Many important types of generative classifiers use Gaussian (also called normal) distributions, either as the model (classifier) distribution itself or as components ("building blocks") for more complex distributions. An n-dimensional Gaussian distribution is parameterized by an n-dimensional mean and an n-by-n-dimensional covariance matrix. Thus, for one-dimensional distributions, the mean and covariance are both one-dimensional, but for a ten-dimensional distribution, the mean is a ten-dimensional vector and the covariance is a 10-by-10 matrix. For this reason, the storage requirements for working with high-dimensional Gaussian distributions increase with the square of the dimension. Representing the full covariance of high-dimensional Gaussian distributions can be prohibitively expensive for embedded applications.

Whether a class probability density function is modeled using a single Gaussian or by a more complex combination of Gaussian components (as is used in mixture models or hidden Markov Models) important reductions in model storage and computational complexity can be gained by using a homoschedastic, as opposed to a heteroschedasitic representation of the model variance.

The heteroschedastic representation of model variance is the conventional n-by-n covariance matrix. The diagonal terms of this matrix capture how each of the n features varies independently of the other features, and the off-diagonal terms capture the correlations (positive or negative) of the variation between each feature and each other feature in the model.

For Gaussian distributions in which the features vary independently, the off-diagonal terms will be small or zero. For distributions in which features are strongly correlated, the off-diagonal terms can be quite large, and hence important for modeling the distribution.

One way to work with Gaussian distributions is to assume that all off-diagonal terms are zero—this is a so-called homoschedastic distribution. If the features are actually independent, this will be a good approximation of the original heteroschedastic distribution, and will reduce the storage requirements to represent the distribution from $\Theta(n^2)$ to $\Theta(n)$—a substantial improvement for embedded implementations. If the off-diagonal terms are not small, then the resulting homoschedastic distribution will not be a good approximation of the original heteroschedastic distribution.

The use of PCA for dimensionality reduction (as described below) transforms features into a factor space with little or no correlation, hence making homoschedastic representation generally more appropriate.

Windowing, Feature Computation and Dimensionality Reduction

In this section, the related topics of windowing, feature computation, and dimensionality reduction are discussed. Methods of preliminary digital signal processing and analysis simplify classification and reduce the internal bandwidth of the classification process.

Those skilled in the art may note that a separate digital signal processing or digital filtering step is not included. This is because separate digital signal processing for signal smoothing and noise reduction operations is not necessary if the previously described band-limiting and analog filtering techniques have been properly implemented. By eliminating DSP signal conditioning from the classification information processing chain substantial processing power consumption reductions are realized, with the attendant reductions in size, weight, cost, etc. DSP operations that are not related to signal conditioning are considered part of the feature computation process, as described below.

Windowing

The first step in the digital processing of sensor data for classification is windowing. Windowing is the process by which a sequence of samples are grouped together in a single chunk or vector. Depending on the number of samples and sampling rate, the resulting feature vector will capture the dynamic behavior of the signal over some period of time, which is referred to as the "window." The window may be defined either in terms of duration (a one-second window, for instance) or number of samples (a 64 sample window). Because the time-varying properties of interest might fall between non-overlapping windows, it is often (though not universally) desirable to have windows overlap by 50%.

Feature Computation

Classification is about discerning salient differences between signals, or collections of signals. Often these differences are subtle, and often relate to the dynamic or time-varying nature of the signals in question. In order to reduce the complexity of the classification process it is frequently desirable to transform the original signal(s) into a derived form that makes differences between classes more apparent. This process of transforming the original signal into a more appropriate form for classification is called feature computation. The choice of appropriate feature computation is important to reducing the complexity of the classification process, and hence important to implementing the classification system with minimal size, power consumption, and cost.

In this section, a few important methods for computing features are described, but one skilled in the art will recognize that there are any number of possible variations on these methods. This list is intended to be representative, not exhaustive.

Frequency Domain Transformation

A useful type of vector feature computation is transforming into or out of a frequency domain representation using the DFFT, or discrete fast Fourier transform. If salient differences between classes are to be found in dynamic behavior operating on a relatively short time-scale, windowing followed by frequency domain transformation can simplify the classification process a great deal. In particular, computing the power spectrum (the magnitude square of the DFFT) is often a useful feature computation operation for classifying time-varying signals.

FIR and IIR filtering

In general, signal conditioning is performed in the present embodiments in analog prior to digital sampling. A more complex, application-specific digital filtering is often useful for feature computation. More complex filters can easily be implemented digitally in the form of finite impulse response (FIR) and infinite impulse response (IIR) filtering. Multiple filters may be applied to the same signal or signals, which in turn might be grouped to produce a vector signal.

An important class of FIR filter is the matched filter, the response of which can play an important role in a wide range of time-domain based signal classification tasks. One can detect the presence of specific time-domain patterns in a signal by convolution with an appropriate matched filter.

Standard Vector Operations

The result of windowing or other feature computation operations is a signal of vectors. Standard vector operations, such as projection, magnitude calculation, linear transformation, numerical integration or differentiation, convolution, etc., which are a part of other specified techniques may be useful in their own right.

Dimensionality Reduction

After feature computation the next step is dimensionality reduction. It is not uncommon for feature signals to have dozens, or even hundreds of dimensions. Frequently, however, not all of those dimensions are equally useful in discerning one class from another. Furthermore, the use of higher-dimensional features in classification calls for correspondingly higher-dimensional classification calculations, which in turn call for the storage of higher-dimensional classifier parameters.

The storage and computational requirements for working with higher-dimensional features can be a significant problem in engineering light-weight real-time classification systems. In many cases it is possible to gain the benefits of working with higher-dimensional features while performing classification calculations in a much lower-dimensional "factor space." The process of going from a higher-dimensional feature space to a lower dimensional factor space is called dimensionality reduction.

The process of dimensionality reduction involves the projection, or mapping, of a high-dimensional feature vector f into a lower dimensional factor space, resulting in a lower-dimensional factor vector f'. If this process is well designed, the resulting factor vector f' will contain nearly as much useful information as the original feature vector f, but with less extraneous information and fewer terms. For example, a 64-dimensional feature vector might be "distilled" through dimensionality reduction into an 8-dimensional factor vector, requiring only 1/8th the original storage. Furthermore, subsequent classification calculations will require 1/8th (or less) storage and calculation.

Dimensionality reduction is typically accomplished through a linear projection operation. Those skilled in the art will understand that non-linear dimensionality reduction operations are possible, but the most common and important methods of dimensionality reduction—PCA, LDA, and HDA—are based on linear projection operations. Hence, this discussion assumes a linear mapping.

In linear projection dimensionality reduction, each factor vector component is a linear combination of feature vector components. Given an n-dimensional feature vector $\vec{f}$ and an m-dimensional factor vector $\vec{f}'$ where m<n, each component $\vec{f}'_i$ is computed as an inner product of $\vec{f}$ and factor weight vector $G_i$ (the i-th row of m row by n column factor weight matrix G). In vector terms this may be written as $$\vec{f}'_i = \vec{f} \cdot G_i \forall 1 \leq i \leq m,$$

or more concisely in matrix form as $$\vec{f}' = G \vec{f}.$$

If the factor weights are chosen properly, a classifier operating on a small number of factors may provide accuracy equivalent or better than a similar classifier using the original high-dimensional feature vector—and at a fraction of the computation and storage cost.

Dimensionality reduction is generally important for lightweight classification implementations. In many cases, it may be possible to reduce the dimensionality of features by a factor of two to five without any loss of classification accuracy, and in some cases a reduction of ten times or greater is possible.

Dimensionality reduction is generally only useful if the factor weight matrix G is chosen well, which is to say chosen so that the dimensionality reduction calculation distills the useful information out of the larger feature space into the smaller factor space. Those skilled in the art will understand that there are several techniques by which G may be chosen, including Principle Component Analysis (PCA), Linear Discriminant Analysis (LDA), and the hybrid PCA/LDA approach known as HDA.

Once factors are computed, they become another type of feature for input into the model evaluation (classification) step.

Model Evaluation

After features are computed and dimensionality is reduced, the resulting factor vector is handed off to the model system for evaluation. Model systems may operate on one or more sets of factors resulting from a plurality of sensor signals and feature computation chains.

Model evaluation can be a complex and expensive operation. Model type and complexity must be chosen carefully to balance the expressive power of the model with the constraints of the real-time implementation. By giving careful attention to all of the steps leading up to model evaluation it is possible to substantially reduce the complexity of the model required for accurate classification, allowing for simpler, more robust model evaluation. As those skilled in the art will appreciate, simpler models are not only easier to implement and faster to evaluate, they are faster to train and less prone to over fitting.

Model types suitable for real time classification applications include Gaussian mixture models, Hidden Markov Models (HMMS), Support Vector Machines (SVMs), decision trees such as those produced through the C4.5 technique, and multi-level model systems such as Markov classification operating on the component-posterior output of Gaussian mixture models. Those skilled in the art will understand that this list is representative, not exhaustive.

Generative (Bayesian) Classification vs. Discriminative (Non-Statistical) Classification There are many different approaches to real-time classification, and many different classification techniques. In this disclosure, the focus is on methods for implementing modern statistical classification algorithms. These techniques can be divided into discriminative and generative techniques.

Discriminative techniques are "black box" techniques in which the classifier discriminates between classes, but does not compute true class posterior probabilities. For example, a multi-hidden-layer neural network may be trained to distinguish between healthy and sick liver tissue samples based on a digital microscope photograph, but cannot assign a probability or confidence to this distinction. Metaphorically speaking, discriminative techniques provide only a "thumbs up" or "thumbs down" assessment for each class under consideration.

Generative techniques are "white box" techniques in which the classification process assigns normalized probabilities to each class. Also called Bayesian techniques, generative classifiers assign normalized posterior probabilities to all classes under consideration, allowing for principled decision making based on the confidence of the classification results. Generative techniques are not necessarily more accurate than discriminative techniques, but are more useful for subsequent inference and decision-making. For example, there is an important difference between being 51% sure that a liver tissue sample is diseased and 99% sure that a liver tissue sample is diseased. A generative classifier will provide the percentage confidence of the classification, whereas a discriminative classifier would say "diseased" in either case.

Figure 11:
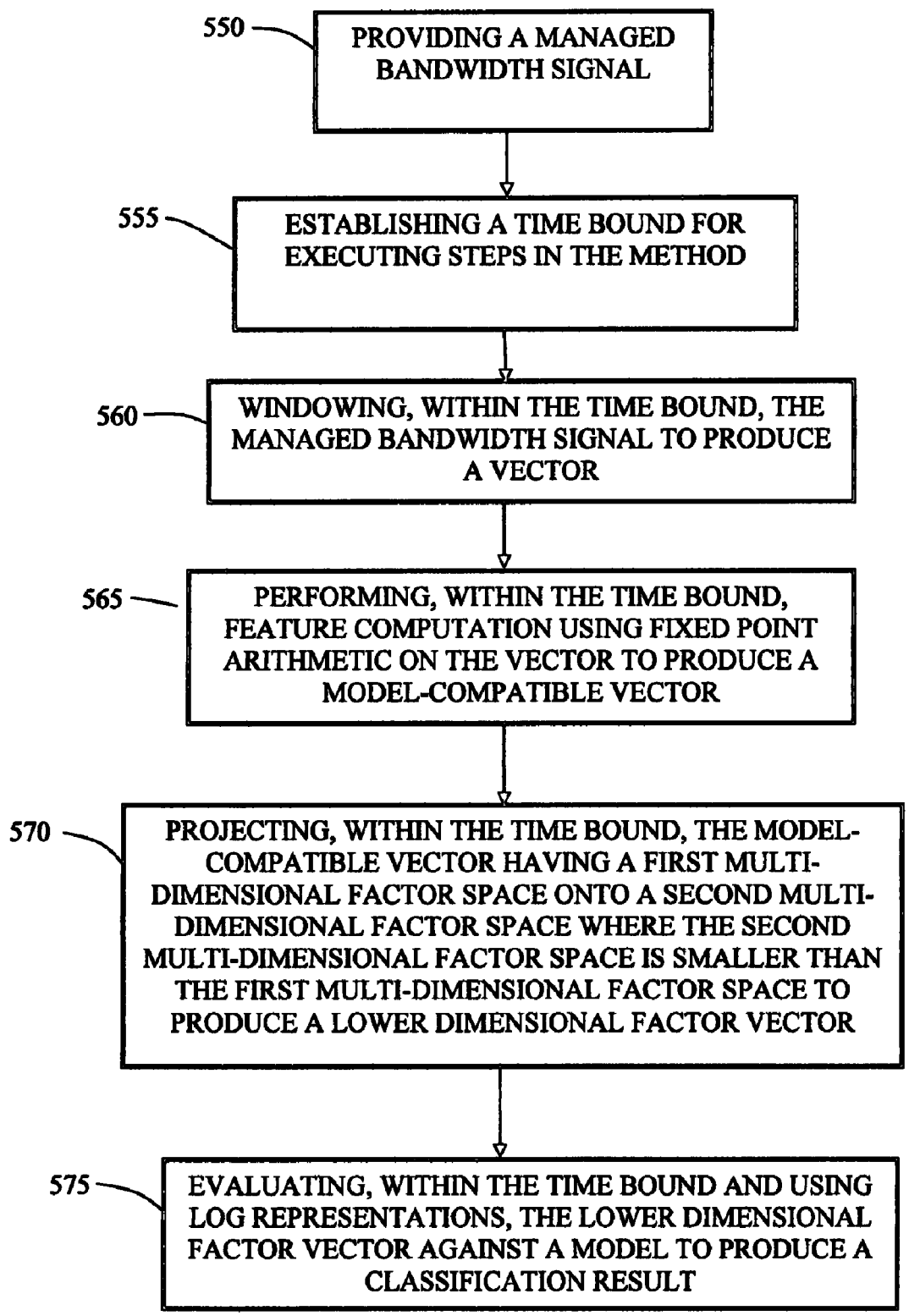
FIG. 11 is a flow chart of the method of statistical classification of the present invention.

FIG. 11 is a flow chart of a method of real-time classification according to principles of the invention and suitable for execution in the system of FIG. 5.

At step 550, the system provides a managed bandwidth signal for real-time classification. Methods of receiving various transducer signals and transforming the received signals into managed bandwidth signals is described below with regard to FIG. 12. As described above, the managed bandwidth signal is a transducer signal processed to limit bandwidth and focused on the portion of the received signal having data of interest to the classification. Managing signal bandwidth increases the efficiency of the classification process and enables the present method to execute successfully on low power and otherwise limited computing resources.

At step 555, the system sets a time bound for execution of each of the following steps of the present method. That is, each of the following steps is executed in a limited period of time, that period of time not to exceed the time bound. This is another factor enabling the successful operation of the real-time classification process on lower power and otherwise limited computing resources.

At step 560, the managed bandwidth signal is windowed. In windowing, as described above, the system processes the received signal taking a sequence of samples and grouping them together to produce single chunk or vector. This step is executed in a period no longer than the time bound of step 555. Windowing is another factor enabling the successful efficient operation of the real-time classification process.

At step 565, the system performs feature computation on the vector produced from the windowing step. Feature computation as described above involves transforming the vector produced by the windowing step into a model-compatible vector. The computations in this step are performed using fixed-point arithmetic. This step is executed within the time bound set by the system and produces a model-compatible vector. Model-compatible means selecting those features of the vector or transforming the vector from one domain into another domain such that a simplest model may be used for the evaluation step (step 575 below). Feature computation and the use of fixed-point arithmetic are additional factors that increase the efficiency of the classification process and enable the present method to execute successfully on low power and otherwise limited computing resources.

At step 570, the system projects, within the time bound, the model-compatible vector having a first multi-dimensional factor space onto a second multi-dimensional factor space where the second multi-dimensional factor space is smaller than the first multi-dimensional factor space to produce a lower dimensional factor vector. Projection further increases the efficiency of the classification process.

At step 575, the system performs an evaluation of the lower dimensional factor vector against a model. The evaluation step produces a classification result. The present method involves only a single factor, however, in alternative embodiments, the system operates on a plurality of signals and ultimately provides a plurality of lower dimensional factor vectors to the modeling step, the plurality of factors resulting from a plurality of sensor signals and feature computation chains. Model evaluation can be a complex and expensive operation however this step like the other described above is executed within the time bound set by the system. Model type and complexity is selected to balance the expressive power of the model with the constraints of the real-time implementation. The computations in this step are performed using fixed point arithmetic and also log representations in order to perform the computations as efficiently as possible thereby enabling the present method to execute successfully on limited computing resources.

An example implementation of the process described above is the classification of an accelerometer signal in order to determine whether a person wearing the system of the present invention is walking or running. A model is developed and stored in the system. The system takes the accelerometer signals and transforms the signal as described in the process above. The factor produced by the signal processing steps is then classified using the model and the classification result provides for example an output that states that the person is walking or running or alternatively, provides a probability of walking or a probability of running.

Figure 12:
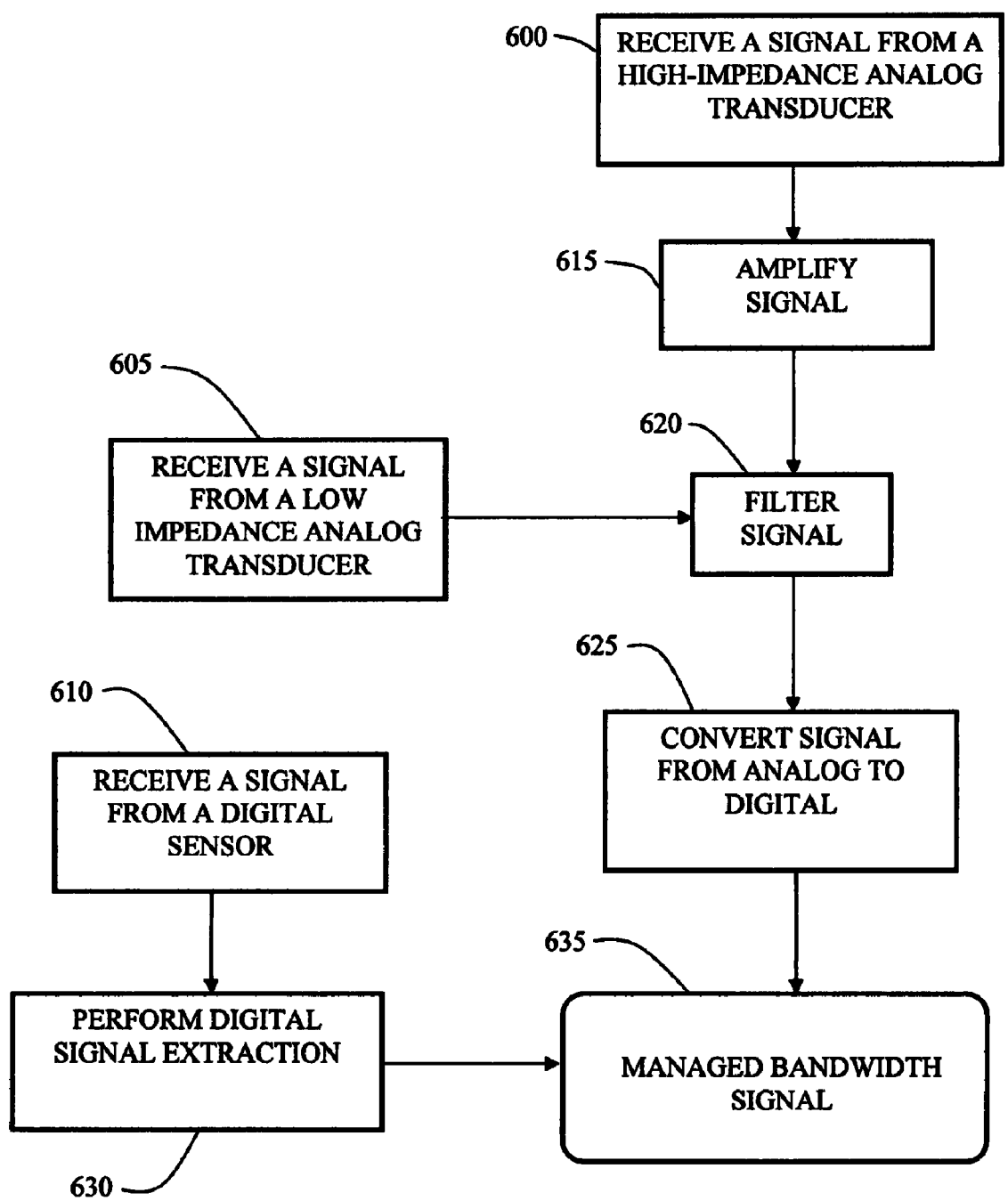
FIG. 12 is a flow chart of the method of signal conditioning according to principles of the invention.

FIG. 12 shows a process of producing a managed bandwidth signal according to principles of the invention. The process is suitable for execution on the system of FIG. 5. Much of the detail of producing a managed bandwidth signal is also described above in the: Signal Filtering, Sampling Rate, and Sampling Precision" section.

The initial signal, in this embodiment, is received from one of three sources, a high impedance analog transducer, step 600, a low impedance analog transducer, step 605 or a digital sensor, step 610.

If the signal is received from a high-impedance analog transducer, the signal is amplified, step 615 and then filtered step 620. Both of these operations are described above. If the signal is received from a low impedance analog transducer, the signal is filtered step 620. At step 625, the analog signals are converted to digital signals resulting in managed bandwidth signals 635. If the signal is received from a digital sensor, digital signal extraction is performed on the signal at step 630 to produce a managed bandwidth signal 635.

Those skilled in the art will understand that there are advantages and disadvantages to both generative and discriminative techniques. Most of the techniques taught in this disclosure are relevant to the development and implementation of both generative and discriminative techniques. Modern machine learning has focused on the development of generative classification techniques, and there is a growing consensus that the use of generative techniques is preferable for most applications.

It is to be understood that the above-identified embodiments are simply illustrative of the principles of the invention. Various and other modifications and changes may be made by those skilled in the art which will embody the principles of the invention and fall within the spirit and scope thereof.

We claim:

1. A method for real-time signal classification, the method to be executable on a low-power processor, the method comprising:

providing a managed bandwidth signal from an accelerometer sensor;

establishing, by a processor, a time bound for executing steps in the method;

windowing, by the processor, within the time bound, the managed bandwidth signal to produce an acceleration vector based on an acceleration model;

performing, by the processor, within the time bound, feature computation using fixed point arithmetic on the vector to produce a model-compatible acceleration vector based on the acceleration model;

projecting, by the processor, within the time bound, the model-compatible acceleration vector having a first multi-dimensional factor space onto a second multi-dimensional factor space where the second multi-dimensional factor space is smaller than the first multi-dimensional factor space to produce a lower dimensional factor vector; and evaluating, by the processor, within the time bound and using log representations, the lower dimensional factor vector against the acceleration model to produce a classification result.

2. The method of claim 1 wherein the step of providing a managed bandwidth signal further comprises:

receiving, by the processor, a signal from an analog acceleration sensor; and filtering, by the processor, the signal to place a limit on the frequency of the signal.

3. The method of claim 2 wherein the filtering step further comprises shifting, by the processor, a center point of the signal.

4. The method of claim 2 wherein the filtering step further comprises scaling, by the processor, the amplitude of the signal.

5. The method of claim 1 wherein the step of providing a managed bandwidth signal further comprises:

receiving, by the processor, a data from a digital acceleration sensor; and filtering, by the processor, the data to produce the managed bandwidth signal.

6. The method of claim 1 wherein the windowing step further comprises grouping, by the processor, a sequence of samples to form an acceleration vector that represents dynamic motion behavior of the signal over time.

7. The method of claim 1 wherein the step of performing feature computation further comprises transforming, by the processor, the acceleration vector from a time domain to a frequency domain.

8. The method of claim 1 wherein the step of performing feature computation further comprises digitally filtering, by the processor, the acceleration vector.

9. The method of claim 1, wherein projecting within the time bound, the model-compatible acceleration vector further comprising projecting, by the processor, within the time bound, the model-compatible acceleration vector having the first multi-dimensional factor space onto the second multi-dimensional factor space based on a lowest sampling resolution for the acceleration model, where the second multi-dimensional factor space is smaller than the first multi-dimensional factor space to produce a lower dimensional factor vector.

10. A system for real-time signal classification, the system having a lower power processor, the system comprising:
    means for providing a managed bandwidth signal from an accelerometer sensor;
    means for establishing a time bound for execution of classification processing in the system;
    means for windowing, within the time bound, the managed bandwidth signal to produce an acceleration vector based on an acceleration model;
    means for performing, within the time bound, feature computation using fixed point arithmetic on the acceleration vector to produce a model-compatible acceleration vector based on the acceleration model;
    means for projecting, within the time bound, the model-compatible acceleration vector having a first multi-dimensional factor space onto a second multi-dimensional factor space where the second multi-dimensional factor space is smaller than the first multi-dimensional factor space to produce a lower dimensional factor vector; and
    means for evaluating, within the time bound and using log representations, the lower dimensional factor vector against the acceleration model to produce a classification result.

11. The system of claim 10 wherein the means for providing a managed bandwidth signal further comprises:
    means for receiving a signal from an analog acceleration sensor; and
    means for filtering the signal to place a limit on the frequency of the signal.

12. The system of claim 11 wherein the means for filtering further comprises means for shifting a center point of the signal.

13. The system of claim 11 wherein the means for filtering further comprises means for scaling the amplitude of the signal.

14. The system of claim 10 wherein the means for providing a managed bandwidth signal further comprises:
    means for receiving data from a digital acceleration sensor; and
    means for filtering the data to produce the managed bandwidth signal.

15. The system of claim 10 wherein the means for windowing further comprises means for grouping a sequence of samples to form an acceleration vector that represents dynamic motion behavior of the signal over time.

16. The system of claim 10 wherein the means for performing feature computation further comprises means for transforming the acceleration vector from a time domain to a frequency domain.

17. The system of claim 10 wherein the means for performing feature computation further comprises means for digitally filtering the vector.

18. The system of claim 10 wherein the means for performing feature computation further comprises means for computing time derivatives of the acceleration vector.

19. The system of claim 10 wherein the means for performing feature computation further comprises
    means for performing vector additions, vector products, and vector scaling operations, and
    means for computing vector magnitudes.

20. The system of claim 10, wherein the classification result is indicative of a motion of a person.

* * * * *